(12) United States Patent
Hastwell et al.

(10) Patent No.: US 8,969,008 B2
(45) Date of Patent: Mar. 3, 2015

(54) GENOTOXIC TESTING

(71) Applicant: Gentronix Limited, Manchester (GB)

(72) Inventors: Paul Hastwell, Bedfordshire (GB);
Richard Walmsley, Marple (GB)

(73) Assignee: Gentronix Limited (GB)

( * ) Notice: Subject to any disclaimer, the term of this patent is extended or adjusted under 35 U.S.C. 154(b) by 0 days.

(21) Appl. No.: 13/860,061

(22) Filed: Apr. 10, 2013

(65) Prior Publication Data
US 2013/0316362 A1 Nov. 28, 2013

Related U.S. Application Data

(63) Continuation of application No. 11/596,766, filed as application No. PCT/GB2005/001913 on May 18, 2005, now abandoned.

(30) Foreign Application Priority Data

May 20, 2004 (GB) .................................. 0411198.5

(51) Int. Cl.
*C12Q 1/68* (2006.01)
*C12N 15/85* (2006.01)
*G01N 33/50* (2006.01)

(52) U.S. Cl.
CPC .............. *C12Q 1/6897* (2013.01); *C12N 15/85* (2013.01); *G01N 33/5008* (2013.01); *C12N 2830/002* (2013.01)
USPC ........................................ 435/6.19; 435/6.13

(58) Field of Classification Search
CPC ...... C12N 15/85; C12N 15/00; C12Q 1/6897; C12Q 1/00
USPC ...................... 435/6.13, 320.1, 366
See application file for complete search history.

(56) References Cited

U.S. PATENT DOCUMENTS

| | | |
|---|---|---|
| 6,523,041 B1 | 2/2003 | Morgan et al. |
| 2001/0007768 A1 | 7/2001 | Howell et al. |
| 2002/0072076 A1 | 6/2002 | Sakamoto et al. |
| 2003/0049690 A1 | 3/2003 | Walmsley et al. |
| 2003/0134288 A1 | 7/2003 | Li et al. |
| 2005/0202518 A1 | 9/2005 | Vedrine et al. |
| 2007/0224609 A1 | 9/2007 | Hastwell et al. |

FOREIGN PATENT DOCUMENTS

| | | |
|---|---|---|
| JP | 09-005324 A | 1/1997 |
| JP | 09-121892 A | 5/1997 |
| WO | 98/44149 A1 | 10/1998 |
| WO | 2005/113802 A2 | 12/2005 |

OTHER PUBLICATIONS

Van Gompel et al., Mutagenesis, 20(6): 449-454, Nov. 15, 2005.*
Giuliano et al., American Chemical Society, 33-37, 2003.*
Akyuz et al. Altex 20: 77-84, 2003.*
Knight et al., Biophotonics International, pp. 1-6, 2001.*
Akutsu et al., "Regulation of Gene Expression by 1a, 25-Dihydroxyvitamin D3 and Its Analog EB1089 Under Growth-Inhibitory Conditions in Squamous Carcinoma Cells," Molecular Endocrinology, vol. 15, No. 7,Jul. 2001, pp. 1127-1139.
Hisatake, Jun-ichi, et al, "Down-Regulation of Prostate-specific Antigen Expression by Ligands for Peroxisome Proliferator-activated Receptor g in Human Prostate Cancer", Cancer Research, vol. 60, pp. 5494-5498, Oct. 1, 2000.
Hollander, M. Christine, et al., "Analysis of the Mammalian gadd45 Gene and Its Response to DNA Damage", The Journal of Biological Chemistry 1993, vol. 268, pp. 24385-24393.
Jiang, Feng, et al., "G2/M Arrest by 1 ,25-Dihydroxyvitamin D3 in Ovarian Cancer Cells Mediated through the Induction of GADD45 via an Exonic Enhancer", The Journal of Biological Chemistry 2003, vol. 278, No. 48, pp. 48030-48040.
Juven-Gershon et al., The RNA polymerase II core promoter—the gateway to transcription, Curr Opin Cell Bioi. 20 (3):253-9, 2008.
Kawasaki, Mikiko, et al., "Inducible liver injury in the transgenic rat by expressing liver-specific suicide gene", Biochemical and Biophysical Research Communications, 2003, vol. 311, pp. 920-928.
Kornberg, The molecular basis of eukaryotic transcription, Proc Natl Acad Sci USA. 104(32): 12955-61, 2007.
Liebermann et al. Myeloid differentiation (MyD) primary response genes in hematopoiesis, Oncogene 21 (21):3391-402, 2002.
Newton, et al. The Utility of DNA Microarrays for Characterizing Genotoxicity. Environmental Heath Perspectives, vol. 112, No. 4, pp. 420-422, Mar. 2004.
Ohba' Seigo, et al., "Expression of Hsp47 in Fibroblasts Derived from Fetal and Neonatal Rat Tongues", Jpn J. Oral Biol. 2002, No. 44, pp. 541-548.
Sharp, Split genes and RNA splicing, Cell 77: 805-815, 1994.
Todd et al., The CAT-Tox (L) assay: a sensitive and specific measure of stress-induced transcription in transformed human liver cells, Fundam Appl Toxicol. 28(1 ):118-28, 1995.
Zhao hui, Yang, et al., Chinese Journal of Experimental Surgery, Mar. 2005, vol. 22, No. 3, pp. 328-331, English abstract on p. 328.
Zheng et al., "Inhibition of NF-KB Stabilizes gadd45a mRNA," Biomedical and Biophysical Research Communications, vol. 329, No. 1, Apr. 2005, pp. 95-99.

(Continued)

*Primary Examiner* — Thaian N Ton
(74) *Attorney, Agent, or Firm* — Lerner, David, Littenberg, Krumholz & Mentlik, LLP

(57) ABSTRACT

The present invention relates to methods for detecting for the presence of an agent that putatively causes or potentiates DNA damage comprising subjecting a cell (containing a DNA sequence encoding a reporter protein operatively linked to a human GADD45α gene promoter and a human GADD45α gene regulatory element arranged to activate expression of the DNA sequence in response to DNA damage) to an agent; and monitoring the expression of the reporter protein from the cell. The invention also concerns expression cassettes, vectors and cells which may be used according to such a method and also modified media that may be employed in fluorescence assays and in preferred embodiments of the method of the invention.

10 Claims, 16 Drawing Sheets

(56) References Cited

OTHER PUBLICATIONS

Database EMBL [Online] Sep. 21, 2002, "Luciferase, fluorescent protein, nucleic acids encoding luciferase and fluorescent protein and utilization thereof in diagnosis, high-process screening and novel item." XP002594520 retrieved from EBI accession No. EMBL:BD137234.

Database Geneseq [Online] Aug. 7, 2008, "Humanized Gaussia princeps luciferase (hGLuc) coding sequence, Seq ID 3." XP002594519.retrieved from EBI accession No. GSN:ARW46012 Database accession No. ARW46012.

Hastwell P W et al: Mutation Research. Genetic Toxicology and Environmentalmutagenesis, Elsevier, Amsterdam, NL, 607(2);160-175 (2006), XP025175734.

International Search Report, PCT/GB2010/000581, dated Sep. 17, 2010.

Kienast et al. (Blood 1990. vol. 75, No. 1, pp. 116-121).

Liebermann Dan A et al: Journal of Molecular Signaling, Biomed Central Ltd, 3(1); 15 (2008), XP021045430.

Tannous B A et al, Molecular Therapy, Academic Press, San Diego, CA, 11(3); 435-443 (2005), XP004757251.

Targeting Systems: "Gaussia Luciferase Assay System", Internet Citation Jan. 1, 2005, XP002392448 Retrieved from the Internet: URL:http://www.targetingsystems.com/gaussia_luciferase_product_brochure20 05.pdf [retrieved on Jan. 1, 2006].

Wu Chun et al: Biotechniques, Informa Life Sciences Publishing, Westborough, MA, US, 42(3): 290-292 (2007), XP009136932.

\* cited by examiner

A

B

GENOTOXIC TESTING

CROSS-REFERENCE TO RELATED APPLICATIONS

The present application is a continuation of U.S. patent application Ser. No. 11/596,766, filed on Nov. 16, 2006, which application is a national phase entry under 35 U.S.C. §371 of International Application No. PCT/GB2005/001913 filed May 18, 2005, which claims priority from 0411198.5 filed May 20, 2004, all of which are incorporated herein by reference.

SEQUENCE LISTING

The instant application contains a Sequence Listing which was submitted in ASCII format via U.S. Postal Service on Nov. 16, 2006, in the parent application, Ser. No. 11/596,766, and is hereby incorporated by reference in its entirety.

BACKGROUND OF THE INVENTION

The present invention relates to methods for detecting agents that cause or potentiate DNA damage, and to molecules and transfected cell lines that may be employed in such methods. In particular, the invention relates to biosensors for detecting DNA damage in human cell cultures.

DNA damage is induced by a variety of agents such as ultraviolet light, X rays, free radicals, methylating agents and other mutagenic compounds. DNA damage can also be caused indirectly either by agents that affect enzymes and proteins which interact with DNA (including polymerases and topoisomerases) or by promutagens (agents that can be metabolised to become mutagenic). Any of these agents may cause damage to the DNA that comprises the genetic code of an organism and cause mutations in genes. In animals, such mutations can lead to carcinogenesis or may damage the gametes to give rise to congenital defects in offspring. Such DNA damaging agents can be collectively known as genotoxins.

These DNA damaging agents may chemically modify the nucleotides that comprise DNA and may also break the phosphodiester bonds that link the nucleotides or disrupt association between bases (T-A or C-G). To counter the effect of these DNA damaging agents cells have evolved a number of mechanisms. For example, the SOS response in *E. coli* is a well-characterised cellular response induced by DNA damage in which a series of proteins are expressed, including DNA repair enzymes, which repair the damaged DNA. In mammalians, nucleotide excision repair and base excision repair mechanisms play a prominent role in DNA damage repair, and are the primary mechanism for removal of bulky DNA adducts and modified bases.

There are numerous circumstances when it is important to identify what agents may cause or potentiate DNA damage. It is particularly important to detect agents that cause DNA damage when assessing whether it is safe to expose a person to these agents. For instance, a method of detecting these agents may be used as a genotoxicity assay for screening compounds that are candidate medicaments, food additives or cosmetics to assess whether or not the compound of interest induces DNA damage. Alternatively, methods of detecting DNA damaging agents may be used to monitor for contamination of water supplies with pollutants that contain mutagenic compounds.

Various methods, such as the Ames Test, the in vitro micronucleus test and the mouse lymphoma assay (MLA), for determining the toxicity of an agent are known but are unsatisfactory for a number of reasons. For instance, incubation of samples can take many weeks, when it is often desirable to obtain genotoxic data in a shorter time frame. Furthermore, many known methods of detecting DNA damage (including the Ames Test and related methods) assay lasting DNA damage, as an endpoint, either in the form of mis-repaired DNA (mutations and recombinations) or unrepaired damage in the form of fragmented DNA. However, most DNA damage is repaired before such an endpoint can be measured and lasting DNA damage only occurs if the conditions are so severe that the repair mechanisms have been saturated.

An improved genotoxic test is disclosed in WO 98/44149, which concerns recombinant DNA molecules comprising a *Saccharomyces cerevisiaie* regulatory element that activates gene expression in response to DNA damage operatively linked to a DNA sequence that encodes a light emitting reporter protein, such as Green Fluorescent Protein (GFP). Such DNA molecules may be used to transform a yeast cell for use in a genotoxic test for detecting for the presence of an agent that causes or potentiates DNA damage. The cells may be subjected to an agent and the expression of the light emitting reporter protein (GFP) from the cell indicates that the agent causes DNA damage. The genotoxic tests described in WO 98/44149 detect the induction of repair activity that can prevent an endpoint being reached. The method described in WO 98/44149 may therefore be used to detect for the presence of DNA damaging agents.

U.S. Pat. No. 6,344,324 discloses a recombinant DNA molecule comprising the regulatory element of the hamster GADD153 upstream promoter region that activates gene expression in response to a wide range of cellular stress conditions, linked to a DNA sequence that encodes GFP. This reporter system is carried out in a human head and neck squamous-cell carcinoma cell line. However, problems associated with this reporter system are that it requires at least a four day treatment period at test agent concentrations that result in less than 10% cell survival, followed by analysis of fluorescence by flow cytometry. In addition, the biological relevance of any gene induction when tested with agents at this level of toxicity is debatable. Furthermore, this development does not disclose a means of specifically monitoring for the presence of agents that may cause or potentiate DNA damage, and the mechanism of GADD153 induction remains unclear. Hence, this system is of very limited use as a human DNA damage biosensor.

Therefore, it is an aim of embodiments of the present invention to address problems associated with the prior art, and to provide an improved biosensor for detecting DNA damage in human cell cultures.

BRIEF SUMMARY OF THE INVENTION

According to a first aspect of the present invention, there is provided an expression cassette comprising a DNA sequence encoding a reporter protein, which DNA sequence is operatively linked to a human GADD45α gene promoter and a human GADD45α gene regulatory element arranged to activate expression of the DNA sequence in response to DNA damage.

By the term "regulatory element", we mean a DNA sequence that regulates the transcription of a gene with which it is associated, i.e. the DNA sequence encoding the reporter protein.

By the term "operatively linked", we mean that the regulatory element is able to induce the expression of the reporter protein.

According to a second aspect of the invention, there is provided a recombinant vector comprising an expression cassette according to the first aspect.

According to a third aspect of the invention, there is provided a cell containing a recombinant vector in accordance with the second aspect of the present invention.

According to a fourth aspect of the present invention, there is provided a method of detecting for the presence of an agent that causes or potentiates DNA damage comprising subjecting a cell in accordance with the third aspect of the present invention to an agent; and monitoring the expression of the reporter protein from the cell.

The method of the fourth aspect of the invention represents a novel cost-effective genotoxicity screen that may be used to provide a pre-regulatory screening assay for use by the pharmaceutical industry and in other applications where significant numbers of agents or compounds need to be tested. It provides a higher throughput and a lower compound consumption than existing in vitro and in vivo mammalian genotoxicity assays, and is sensitive to a broad spectrum of mutagens.

The method of the fourth aspect of the invention is suitable for assessing whether or not an agent may cause DNA damage. It is particularly useful for detecting agents that cause DNA damage when assessing whether it is safe to expose a person to DNA damaging agents. For instance, the method may be used as a genotoxicity assay for screening whether or not known agents, such as candidate medicaments, pharmaceutical and industrial chemicals, pesticides, fungicides, foodstuffs or cosmetics, induce DNA damage. Alternatively, the method of the invention may be used to monitor for contamination of water supplies, leachates and effluents with pollutants containing DNA damaging agents.

The method of the fourth aspect of the invention may also be used for assessing whether an agent may potentiate DNA damage. For example, certain agents can cause accumulation of DNA damage by inhibiting DNA repair (for instance by preventing expression or function of a repair protein) without directly inflicting DNA damage.

Surprisingly, the use of a human GADD45α gene regulatory element in addition to the human GADD45α gene promoter in the expression cassette according to the first aspect of the invention radically enhances the response of the cassette to genotoxic stress and, hence, DNA damage in the cell according to the third aspect. Advantageously, the cassette can be analysed for expression of the reporter protein within or after only 24 hours simply by assaying for the protein in a test culture. The cells may be subjected to the test agent or compound, and expression of the reporter protein in the cell indicates whether the test agent causes DNA damage.

The inventors have found that DNA encoding a human GADD45α gene promoter and a human GADD45α gene regulatory element may be operatively linked a reporter protein to form a cassette according to the first aspect of the invention and then advantageously used in a genotoxic test according to the fourth aspect of the invention. Such cassettes may comprise the whole of the GADD45α gene (including coding sequences) provided that it is operatively linked to DNA encoding a light emitting reporter. For instance cassettes may be made according to the first aspect of the invention comprising the whole of, or substantially all of, the GADD45α gene (comprising regulatory elements and promoter) with DNA encoding a reporter inserted 3' of the GADD45α promoter (e.g. within the GADD45α coding sequence or at the 3' of the coding sequence) end of the arranged to activate expression of the DNA sequence in response to DNA damage.

Preferably, the human GADD45α gene promoter sequence induces RNA polymerase to bind to the DNA molecule and start transcribing the DNA encoding the reporter protein. It is preferred that the promoter sequence comprises the human GADD45α gene promoter sequence and the 5' untranslated region. The promoter sequence may be obtained from the pHG45-HC plasmid, which is illustrated in FIG. 3. The promoter sequence can be seen in each of the expression cassettes in accordance with the invention in FIG. 9, and the nucleotide sequence of the GADD45α gene promoter is shown as bases 4-2254 in SEQ ID Nos. 1, 2, 3, 4 & 5 in the sequence listing. It will be appreciated that the promoter may comprise each of the bases 4-2254 or alternatively may be a functional derivative or functional fragment thereof. Functional derivatives and functional fragments may be readily identified be assessing whether or not transcriptase will bind to a putative promoter region and will then lead to the transcription of the marker protein. Alternatively such functional derivatives and fragments may be examined by conducting mutagenesis on the GADD45α promoter, when in natural association with the GADD45α gene, and assessing whether or not GADD45α expression may occur.

The regulatory element in the expression cassette according to the invention may comprise sequences downstream of the GADD45α gene promoter sequence. The regulatory element may comprise functional DNA sequences such as those encoding translation initiation sequences for ribosome binding or DNA sequences that bind transcription factors which promote gene expression following DNA damage. The regulatory element in the expression cassette according to the invention may comprise at least one exon of the GADD45α gene. For example, the regulatory element may comprise Exon 1, Exon 2, Exon 3, and/or Exon 4 of the GADD45α gene, or at least a region thereof, or any combination thereof. Hence, the regulatory element may comprise any combination of the four exons of the GADD45α gene, or at least a region thereof.

In a preferred embodiment, the regulatory element comprises at least a region of Exon 1 of the GADD45α gene, and preferably at least a region of Exon 3 of the GADD45α gene, and more preferably, at least a region of Exon 4 of the GADD45α gene. It is especially preferred that the regulatory element comprises all of Exon 1 of the GADD45α gene, and preferably at least a region of Exon 3 of the GADD45α gene, and more preferably, all of Exon 4 of the GADD45α gene.

Preferred regulatory elements are illustrated in the each of the expression cassettes in accordance with the invention in FIG. 9. The nucleotide sequence of Exon 3 of the GADD45α gene is shown as bases 3405-3642 in SEQ ID Nos. 2, 3 & 4 in the sequence listing. The nucleotide sequence of the preferred region of Exon 3 of the GADD45α gene is shown as bases 3503-3642 in SEQ ID No. 4. The nucleotide sequence of Exon 4 of the GADD45α gene is shown as bases 4716-5391 in SEQ ID Nos. 2, 3 & 4 in the sequence listing.

Alternatively, or additionally, the regulatory element may comprise a non-coding DNA sequence, for example, at least one intron of the GADD45α gene. For example, the regulatory element may comprise Intron 1, Intron 2, and/or Intron 3 of the GADD45α gene, or at least a region thereof, or any combination thereof. Hence, the regulatory element may comprise any combination of the three introns of the GADD45α gene, or at least a region thereof.

In a preferred embodiment, the regulatory element in the expression cassette according to the invention comprises at least a region of Intron 3 of the GADD45α gene. Intron 3 of GADD45α is illustrated in FIG. 9, and the nucleotide sequence of Intron 3 of the GADD45α gene is shown as bases 3643-4715 in SEQ ID Nos. 2, 3 & 4 in the sequence listing.

In a preferred embodiment, the expression cassette in accordance with the invention comprises the promoter sequence of the GADD45α gene and also gene regulatory elements found within Intron 3 of the genomic GADD45α gene sequence itself. While the inventors do not wish to be bound by any hypothesis, they believe that Intron 3 of the GADD45α gene, contains a putative p53 binding motif, and that it is this p53 motif which surprisingly enhances the response of the expression cassette to genotoxic stress. The putative p53 binding motif is shown as nucleotide bases 3830-3849 of SEQ ID Nos. 2, 3 and 4.

The inventors also believe that Intron 3 of the GADD45α gene may contain a putative TRE motif, which may encode a AP-1 binding site. The putative TRE motif is shown as nucleotide bases 3879-3885 of SEQ ID Nos. 2, 3 and 4. Hence, while the inventors do not wish to be bound by any hypothesis, they postulate that this putative AP-1 binding site may also contribute to the improved response to genotoxic agents.

It is preferred that the expression cassette comprises at least the p53 binding motif and/or the AP-1 binding motif from Intron 3 of the GADD45α gene.

The regulatory element may comprise a 3' untranslated (UTR) region of the GADD45α gene, the nucleotide sequence of which is shown as bases 4830-5391 in SEQ ID Nos. 2, 3, and 4. While the inventors do not wish to be bound by any hypothesis, they believe that this 3' UTR may be involved with stabilisation of mRNA cassette, and hence, may be surprisingly important when used with the rest of the regulatory element, such as Intron 3.

By the term "reporter protein", we mean a protein which when expressed in response to the regulatory element of the DNA molecule of the invention, is detectable by means of a suitable assay procedure. Preferably, the reporter protein comprises a light emitting reporter protein. The DNA sequence that encodes a light emitting reporter protein may code for any light emitting protein, for example Luciferase or Green Fluorescent Protein. However, it is preferred that the DNA sequence codes for a protein that is substantially fluorescent.

Preferred DNA sequences that encode a light emitting reporter protein code for Green Fluorescent Protein (GFP), and light emitting derivatives thereof. GFP is from the jelly fish *Aequorea victoria* and is able to absorb blue light and re-emits an easily detectable green light and is thus suitable as a reporter protein. GFP may be advantageously used as a reporter protein because its measurement is simple and reagent free and the protein is non-toxic.

Derivatives of GFP include DNA sequences encoding for polypeptide analogues or polypeptide fragments of GFP, which are able to emit light. Many of these derivatives absorb and re-emit light at wavelengths different to GFP found endogenously in *Aequorea victoria*.

For instance, preferred expression cassettes according to the first aspect of the invention comprise a DNA sequence that encodes the human enhanced GFP (hEGFP), also known as GFPmut1 variant of GFP. This consists of the GFP wild type containing a double amino acid substitution of Phe-64 to Leu, and Ser-65 to Thr. The coding sequence of the hEGFP gene also contains more than 190 silent base changes, which correspond to human codon usage preferences relative to the native *Aequorea victoria* sequence. This is particularly advantageous for use in a human DNA damage reporter system. The hEGFP sequence may be obtained from the pEGFP-N1 plasmid (e.g. obtained from Clontech), which is shown in FIG. 1. The hEGFP sequence can be seen in each of the expression cassettes in accordance with the invention in FIG. 9, and the nucleotide sequence of the hEGFP is shown as bases 2550-3278 in SEQ ID Nos. 1, 2, 3, 4 & 5 in the sequence listing.

GFP produces a good quantum yield of fluorescence and matches the output of argon ion lasers used in fluorescence activated cell sorters. Cells according to the third aspect of the invention, which contain DNA molecules coding hEGFP, may be used according to the method of the fourth aspect of the invention.

Hence, preferred expression cassettes according to the invention comprise a human GADD45α gene regulatory element and human GADD45α gene promoter operatively linked to a DNA sequence encoding a GFP, or light emitting derivative or analogues thereof (e.g. YFP etc.). Most preferred expression cassettes comprise a human GADD45α gene promoter operatively linked to a DNA sequence encoding a GFP or light emitting derivative thereof, and Intron 3 of the GADD45α gene.

In a first embodiment, the expression cassette according to the first aspect is preferably 5-31, (the cassette illustrated in FIG. 9 as GD531). The nucleotide sequence of expression cassette 5-31 is shown in the sequence listing as SEQ ID No.2.

In a second embodiment, the expression cassette according to the first aspect is preferably 5-32 (the cassette illustrated in FIG. 9 as GD532). The nucleotide sequence of expression cassette 5-32 is shown in the sequence listing as SEQ ID No.3.

In a third embodiment, the expression cassette according to the first aspect is preferably 5-33 (the cassette illustrated in FIG. 9 as GD533) The nucleotide sequence of expression cassette 5-33 is shown in the sequence listing as SEQ ID No.4.

The recombinant vector according to the second aspect of the present invention may for example be a plasmid, cosmid or phage. Such recombinant vectors are of great utility when replicating the expression cassette. Furthermore, recombinant vectors are highly useful for transfecting cells with the expression cassette, and may also promote expression of the reporter protein.

Recombinant vectors may be designed such that the vector will autonomously replicate in the cytosol of the cell or can be used to integrate into the genome. In this case, elements that induce DNA replication may be required in the recombinant vector. Suitable elements are well known in the art, and for example, may be derived from pCEP4 (Invitrogen, 3 Fountain Drive, Inchinnan Business Park, Paisley, PA4 9RF, UK) pEGFP-N1 (BD Biosciences Clontech UK, 21 In Between Towns Road, Cowley, Oxford, OX4 LY, United Kingdom) or pCI and pSI (Promega UK ltd, Delta house, chilworth Science Park, Southampton SO16 7NS, UK).

Such replicating vectors can give rise to multiple copies of the DNA molecule in a transformant and are therefore useful when over-expression (and thereby increased light emission) of the reporter protein is required. In addition, it is preferable that the vector is able to replicate in human, primate and/or canine cells. It is preferred that the vector comprises an origin of replication, and preferably, at least one selectable marker. The selectable marker may confer resistance to an antibiotic, for example, hygromycin or neomycin. Hence, a suitable element is derived from the pCEP4 plasmid (Invitrogen, 3 Fountain Drive, Inchinnan Business Park, Paisley, PA4 9RF, UK), which is illustrated in FIG. 2.

In a first embodiment, the recombinant vector according to the second aspect is preferably pEP-GD531, as illustrated in FIG. 5.

In a second embodiment, the recombinant vector according to the second aspect is preferably pEP-GD532, as illustrated in FIG. 6.

In a third embodiment, the recombinant vector according to the second aspect is preferably pEP-GD533, as illustrated in FIG. 7.

According to the second aspect of the invention the recombinant vector is incorporated within a cell. It is preferred that the cell is eukaryotic. Such host cells may be mammalian derived cells and cell lines. Preferred mammalian cells include human, primate, murine or canine cells. The host cells may be lymphoma cells or cell lines, such as mouse lymphoma cells. The host cells may be immortalised, for example, lymphocytes.

Preferred host cells are human cell lines. Preferably, the host cells are human cell lines having a fully functional p53, for example, ML-1 (a human myeloid leukaemia cell line with wild-type p53), TK6 (a human lymphoblastoid cell line with wild-type p53). However, host cell lines of WI-L2-NS and WTK1 (both of which are sister lines of TK6 and have mutant p53 proteins) are also envisaged. These cell lines may all be found at the European Collection of Cell Cultures (ECACC General Office, CAMR, Porton Down, Salisbury, Wiltshire, SP4 OJG, United Kingdom).

The inventors have found that TK6 human cells are particularly preferred cell lines for use according to the method of the invention. While the inventors do not wish to be bound by any hypothesis, they believe that TK6 cells are most useful because they have a fully functional p53.

Host cells used for expression of the protein encoded by the DNA molecule are ideally stably transfected, although the use of unstably transfected (transient) cells is not precluded.

Transfected cells according to the third aspect of the invention may be formed by following procedures described in the Example. The cell is ideally a human cell line, for example TK6. Such transfected cells may be used according to the method of the fourth aspect of the invention to assess whether or not agents induce or potentiate DNA damage. GFP expression is induced in response to DNA damage and the light emitted by GFP may be easily measured using known appropriate techniques.

Most preferred cells according to the third aspect of the invention are TK6 cells transformed with the vector pEP-GAD532. These cells are referred to herein as GenTK-T01.

It is also envisaged that the expression cassette according to the invention may be integrated into the genome of a host cell. The skilled technician will appreciate suitable methods for integrating the cassette into the genome. For example, the expression cassette may be harboured on a retroviral vector, which in combination with a packaging cell line may produce helper-free recombinant retrovirus, which may then be introduced into the host cell. The cassette may then integrate itself into the genome. Examples of suitable helper-free retroviral vector systems include the pBabePuro plasmid with the BING retroviral packaging cell line [Kinsella and Nolan, 1996. Episomal Vectors Rapidly and Stably Produce High-Titer Recombinant Retroviruses. Human Gene Therapy. 7:1405-1413.]

The method of the fourth aspect of the invention is particularly useful for detecting agents that induce DNA damage at low concentrations. The methods may be used to screen compounds, such as candidate medicaments, food additives or cosmetics, to assess whether it is safe to expose a living organism, particularly people, to such compounds. Alternatively, the method of the fourth aspect of the invention may be employed to detect whether or not water supplies are contaminated by DNA damaging agents or agents that potentiate DNA damage. For instance, the methods may be used to monitor industrial effluents for the presence of pollutants that may lead to increased DNA damage in people or other organisms exposed to the pollution.

The method of the invention is preferably performed by growing cells transfected with a recombinant vector according to the second aspect of the invention (such as pEP-GD531, pEP-GD532, or pEP-GD533), incubating the cells with the agent which putatively causes DNA damage for a predetermined time and monitoring the expression of the light emitting reporter protein directly from a sample of the cells.

Cells are preferably grown in low fluorescence growth medium. This can obviate the need to wash the cells before measurements are made and therefore reduce the number of steps in the method further. For instance, preferred human cells according to the third aspect of the invention may be grown in a low fluorescent media. Suitable media may be a modified RPMI 1640 media and most preferably contains either low concentrations of, or preferably, no riboflavin or phenol red. The inventors have found that the use of such media is surprisingly useful in assays of fluorescent markers such as GFP. The use of such media reduces the "signal to noise ratio" when measuring fluorescence. Therefore, according to a fifth aspect of the invention there is provided a media that does not contain, or contains reduced levels (relative to standard cell culture media) of riboflavin or phenol red for use in fluorescent assays. Most preferably the media contains no riboflavin and no phenol red.

It is preferred that the media is modified such that it does not contain riboflavin. The use of such a modified media would be counter-intuitive to a skilled person because it would be understood that riboflavin is usually required in media. This is because most cells require riboflavin to be able to grow and survive. The inventors have realised that cells, which have been grown in conventional growth media containing fiboflavin, may be removed from such media; placed in media without riboflavin; and will remain viable for the purposes of conducting a reliable fluorescence assay. Cells left in conventional media (containing riboflavin and/or phenol red) tend to provide less satisfactory fluorescence values when tested according to the method of the fourth aspect of the invention (particularly when the reporter protein is GFP or a derivative thereof).

It is preferred that media is used according to the fifth aspect of the invention when conducting assays according to the fourth aspect of the invention. It is most preferred such media is used when performing a genotoxic test with GFP as the reporter.

A preferred media with low autofluorescence is a modified RPMI 1640 media that does not contain riboflavin or Phenol red. A most preferred media is disclosed in table 1 of Example 1.

Other media that could be modified for low autofluorescence include Dulbecco's Modified Eagle media (D-MEM), F-10 Nutrient mixture (Ham), F-12 Nutrient mixture (Ham), and Fischer's medium (GIBCO, Invitrogen, Paisley, UK). The most appropriate medium may be used for different cell types that could be used as a host for recombinant reporter vectors.

According to a preferred embodiment of the method of the invention TK6 cells may be transfected with pEP-GD531, pEP-GD532, or pEP-GD533, and grown in RPMI medium containing no riboflavin. A putative DNA damaging agent (e.g. a food additive or potential medicament or an agent contained within a water sample or effluent sample) may then be added to the medium containing the cells. The cells are then allowed to grow for a defined period of time after which a sample of the cells is removed and fluorescence measured therefrom.

Suitable methods of fluorescence detection and quantitation will be known to the skilled technician, and a method is described in the Examples. A preferred method of fluorescence detection is described in U.S. Pat. No. 6,509,161. This method is particularly useful when the light emitting report is GFP or a derivative thereof.

According to a preferred embodiment of the method of the invention, fluorescence and absorbance readings may be recorded from TK6 cells transfected with pEP-GD531, pEP-GD532, or pEP-GD533, for example, from the well of a microplate. An example of a suitable microplate is a 96 well, black, clear-bottomed microplates, manufactured by Matrix ScreenMates, Cat. No. 4929, Apogent Discoveries, USA, or Corning (BV, Netherlands: Cat. No. 3651). Fluorescence and absorbance measurements may be recorded using a suitable microplate reader, for example, the Tecan Ultra-384 (Tecan UK Ltd.) microplate reader: excitation 485 nm/emission 535 nm with an additional dichroic mirror (reflectance 320 nm-500 nm, transmission 520 nm-800 nm). Absorbance may be measured through a suitable filter, for example, a 620 nm filter.

Most preferred protocols for conducting the method of the fourth aspect of the invention are described in Examples 1, 3 and 4.

From the fluorescence and absorbance measurements, "brightness values" and fluorescence induction ratios for cells according to the third aspect of the invention can be made as described in the examples.

There is background ("constitutive") expression of GFP from the GADD45α-EGFP constructs, thus the higher the cell density, the more fluorescent the culture. In order to correct for fluorescence increase that is consequent on growth, the fluorescence data (GFP) are divided by absorbance data (cell density) to give 'brightness units', i.e. the measure of average fluorescence per cell. This is independent of culture density. Accordingly, measurement of absorbance may be used primarily for normalisation of fluorescence signals rather than a measurement of the toxicity of the DNA damaging agent. Accordingly, it is envisaged that a secondary assay may be used in conjunction with the absorbance measurement in order to determine toxicity via cell viability or apoptosis. For example, using the Biovison Bioluminescence Cytotoxicity Assay (Biovison Incoperated, 2455-D Old Middlefield Way, Mountain View, Calif. 94043, USA), or the Vybrant® Apoptosis Assay Kit (Molecular probes Inc., 29851 Willow Creek Road, Eugene, Oreg. 97402, USA).

Occasionally, compounds show fluorescence themselves or induce cellular auto-fluorescence. Accordingly, when evaluating increased GFP expression the brightness values of a control cell line is subtracted from the brightness values of a reporter cell line. This removes the interference from the data. It is therefore preferred that methods according to the fourth aspect of the invention employ cells containing control vectors based upon reporter vectors according to the second aspect of the invention. Such control vectors may correspond to the reporter vector, but with a non-sense mutation introduced into the light emitting reporter gene.

The recombinant control vector may preferably be the vectors described as pEP-GD500C or pEP-GD532C, as illustrated in FIGS. 18 and 19 respectively.

Preferred methods according to the fourth aspect of the invention will utilise cells according to the third aspect of the invention (e.g. GenTK-T01) and a control cell line based upon TK6 cells transformed with the vector pEP-GD532C (referred to herein as GenTK-C01).

It will be appreciated that some non-genotoxic compounds can be chemically altered by cellular metabolism. In mammals this process is often called metabolic activation (MA). MA can convert certina non-genotoxic compounds (for example promutagens) into genotoxic compounds. Most frequently MA occurs in the liver. For this reason it is often preferred that genotoxicity tests are adapted such that assays of test compound are carried out in the presence and absence of liver extracts that are capable of metabolising a compound is if it were being metabolised in vivo. Example 4 illustrates a preferred method according to the fourth aspect of the invention which utilises a liver extract (known to the skilled person) called S9. Inclusion of such an extract allows assays to detect compounds that only become genotoxic after passage through the liver.

All of the features described herein (including any accompanying claims, abstract and drawings), and/or all of the steps of any method or process so disclosed, may be combined with any of the above aspects in any combination, except combinations where at least some of such features and/or steps are mutually exclusive.

BRIEF DESCRIPTION OF THE DRAWINGS

Embodiments of the invention will now be further described, by way of example only, with reference to the following Examples and Figures in which.

DETAILED DESCRIPTION

Example 1

The following Example outlines the components that have been used in the construction of a series of GADD45α-EGFP Human cell culture DNA damage biosensors/reporters according to the first and second aspects of the invention. In addition, this Example describes the construction of the biosensors (cells according to the third aspect of the invention), and illustrates how they respond to a genotoxic agent, for example, methanesulphonic acid methyl ester (MMS) when utilised in a method according to the fourth aspect of the invention.

1.1 System Components:

(i) The Promoter—From GADD45α

Figure 3:
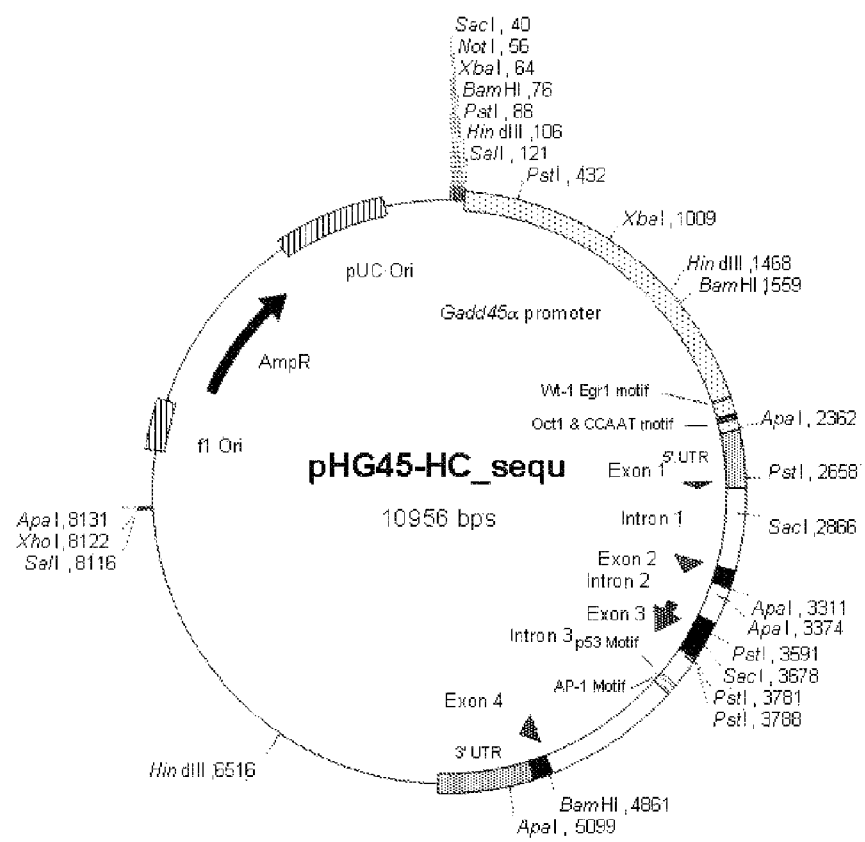
FIG. 3 shows a restriction map of vector pHG45-HC.

The source of the GADD45α promotor is the plasmid pHG45-HC from Albert J. Fornace Jr., M.D. (National Cancer Institute, Building: 37, Room: 6144, National Institutes of Health, Bethesda, Md. 20892, USA), which is illustrated in FIG. 3.

(ii) The Fluorescent Protein—Clontech's EGFP

Figure 1:
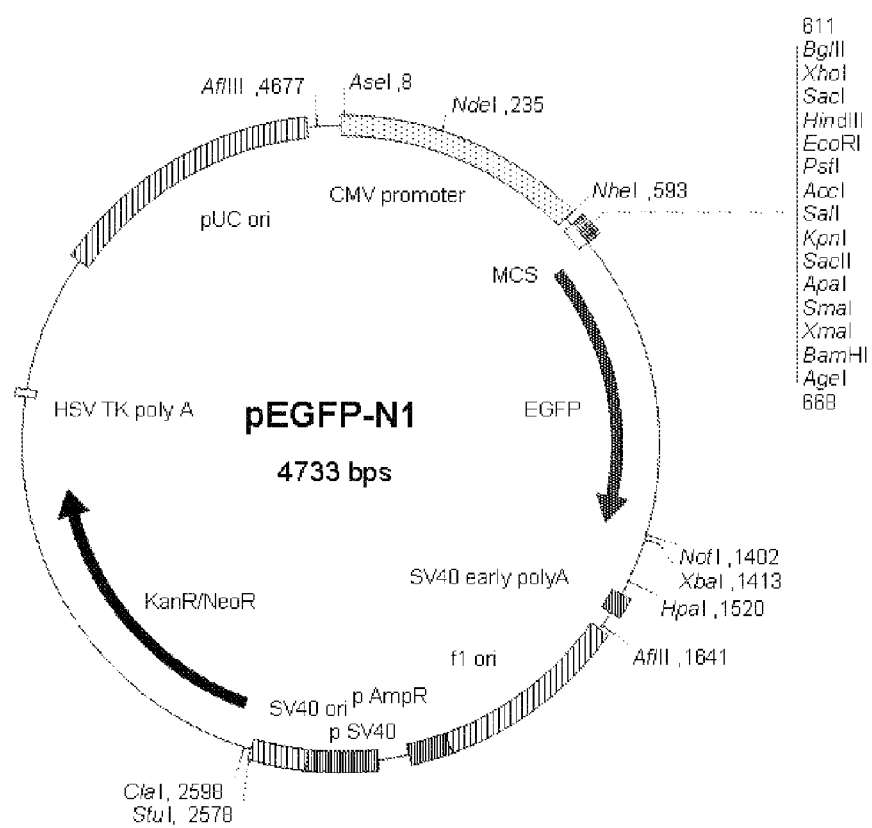
FIG. 1 shows a restriction map of vector pEGFP-N1.

The source of the Green fluorescent protein is the Clontech plasmid pEGFP-N1 (BD Biosciences Clontech UK, 21 In Between Towns Road, Cowley, Oxford, OX4 LY, United Kingdom), which is illustrated in FIG. 1. pEGFP-N1 encodes a red-shifted variant of wild-type GFP that has been optimised for brighter fluorescence and higher expression in mammalian cells. (Excitation maximum=488 nm; emission maximum=507 nm.) The plasmid pEGFP-N1 encodes the GFPmut1 variant, which contains the double-amino-acid substitution of Phe-64 to Leu and Ser-65 to Thr. The coding sequence of the EGFP gene contains more than 190 silent base changes, which correspond to human codon-usage preferences.

1.2 Construction of Biosensor Reporter Cassettes

Figure 2:
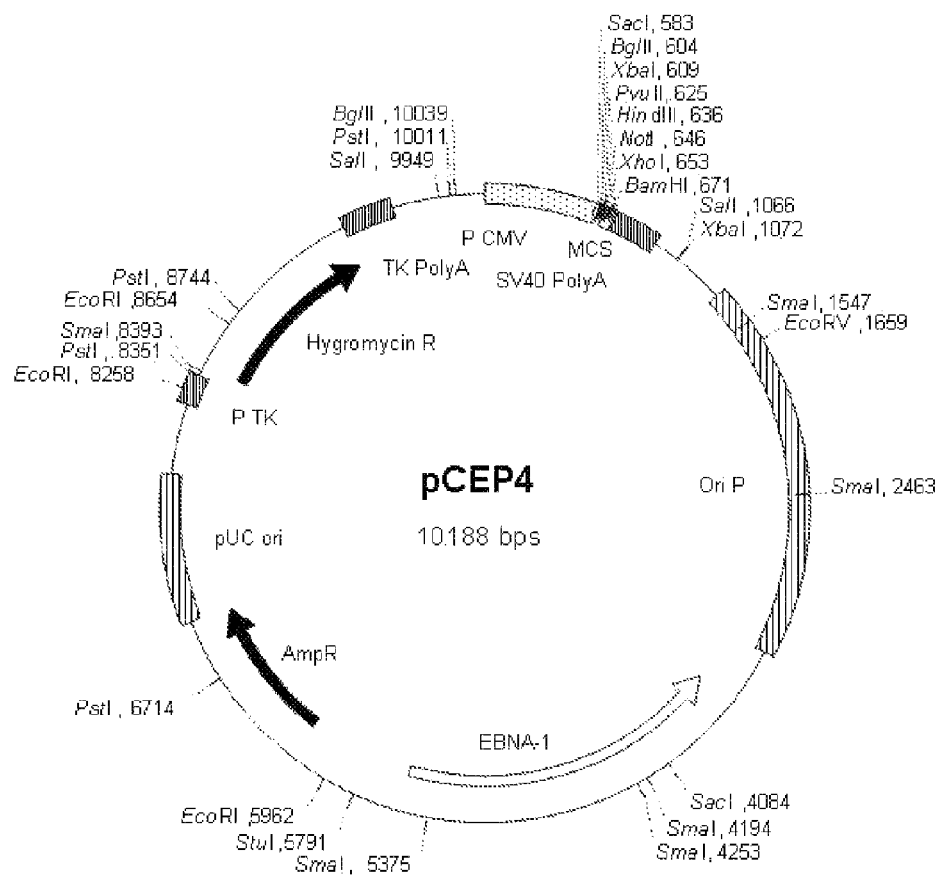
FIG. 2 shows a restriction map of vector pCEP4.

The construction of a set of recombinant vectors each containing a GADD45α-EGFP reporter cassette was carried out in several stages using the Invitrogen pCEP4 plasmid as a backbone, which is illustrated in FIG. 2. Plasmid pCEP4 is an episomal mammalian expression vector that uses the cytomegalovirus (CMV) immediate early enhancer/promoter for high level transcription of recombinant genes inserted into the multiple cloning site. The Epstein-Barr Virus replication origin (oriP) and nuclear antigen (encoded by the EBNA-1 gene) is carried by this plasmid to permit extrachromosomal replication in human, primate and canine cells. pCEP4 also carries the hygromycin B resistance gene for stable selection in transfected cells.

Step 1:

(Insertion of an EGFP module into pCEP4)—An EGFP module (consisting of the Human optimised Green Fluorescent Protein and the SV40 poly adenylation signal) was amplified by PCR from the Clontech plasmid pEGFP-N1 (BD Biosciences Clontech UK, 21 In Between Towns Road, Cowley, Oxford, OX4 LY, United Kingdom), which is shown in FIG. 1. The EGFP gene is flanked by Bgl II-Asc I (5') and Pac I-XhoI (3') sites. This was inserted into Bgl II-Xho I cut pCEP4 (Invitrogen), which is shown in FIG. 2. This step also resulted in the removal of the CMV promoter from pCEP4.

Figure 4:
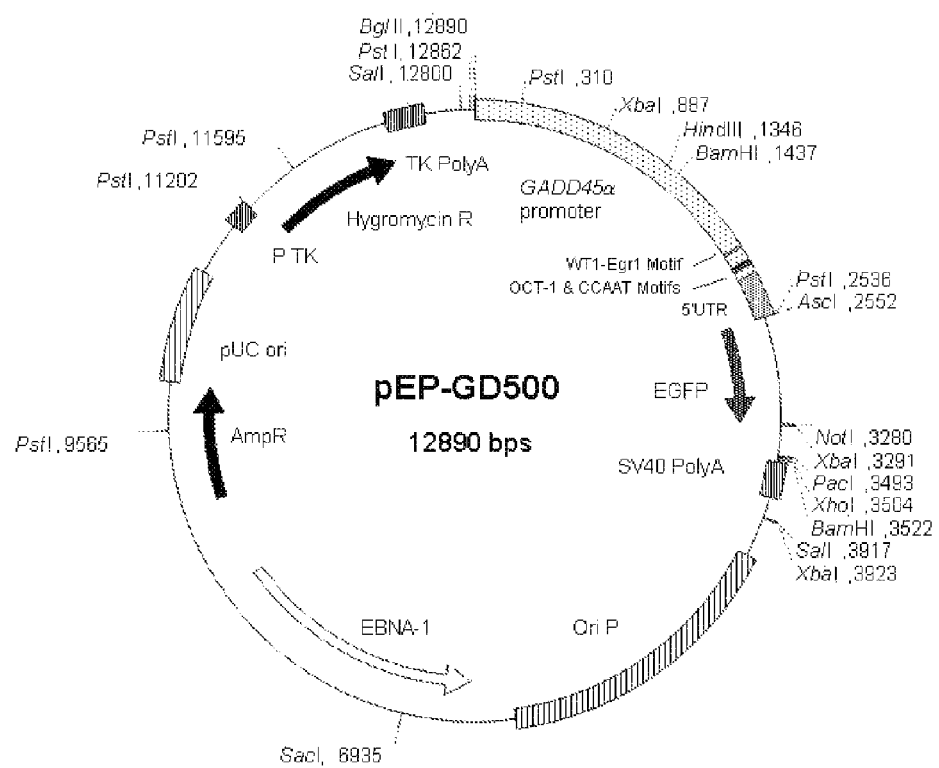
FIG. 4 shows a restriction map of vector pEP-GD500.

Step 2:

(Insertion of GADD45α promoter)—The GADD45α 5' promoter sequence was PCR amplified (from a plasmid pHG45-HC, kindly donated by Albert J. Fornace Jr., M.D. (National Cancer Institute, Building: 37, Room: 6144, National Institutes of Health, Bethesda, Md. 20892, USA), illustrated in FIG. 3, from −2253 bp up to and including the 5' UTR (untranslated region) and start codon (+298 bp) with flanking Bgl II (5') and AscI I (3') sites. This was inserted into the plasmid resulting from step 1. The resultant plasmid was named pEP-GD500, which is shown in FIG. 4.

Step 3:

(Insertion of GADD45α gene sequence)—Various GADD45α gene sequences (3' end of gene) were amplified with cloning sites by PCR and cloned into the plasmid resulting from step 2 (pEP-GD500) to give four further reporter plasmids.

Figure 5:
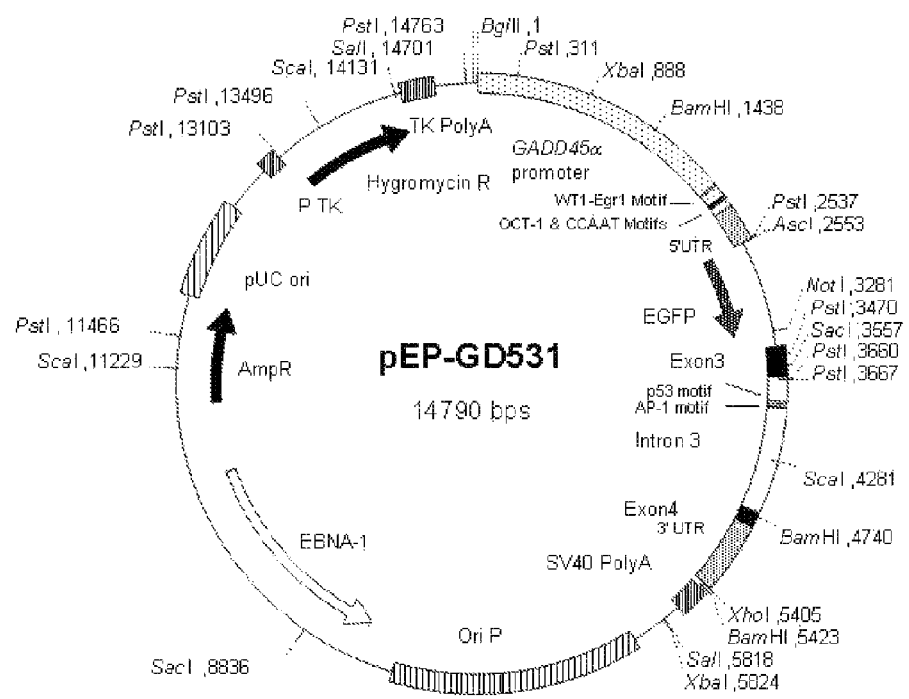
FIG. 5 shows a restriction map of vector pEP-GD531, a preferred recombinant vector according to the present invention.
Figure 6:
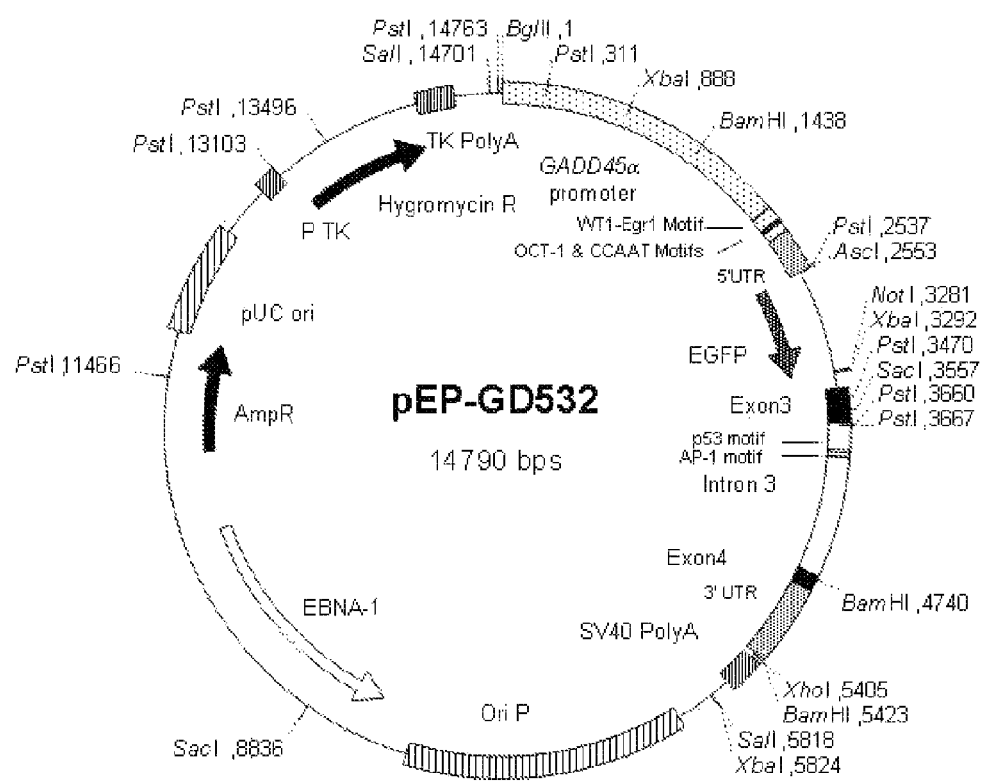
FIG. 6 shows a restriction map of vector pEP-GD532, a preferred recombinant vector according to the present invention.
Figure 7:
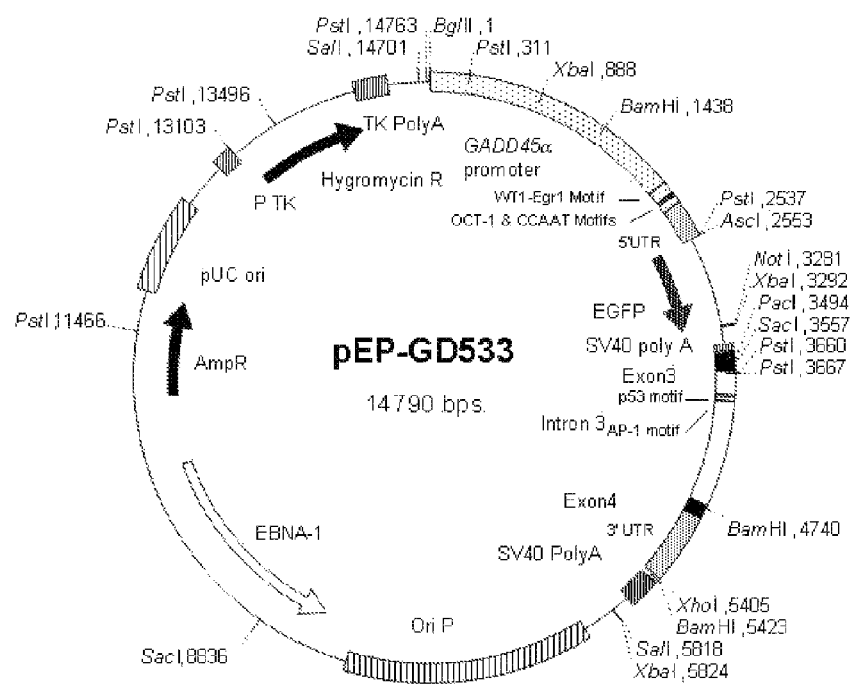
FIG. 7 shows a restriction map of vector pEP-GD533, a preferred recombinant vector according to the present invention.
Figure 8:
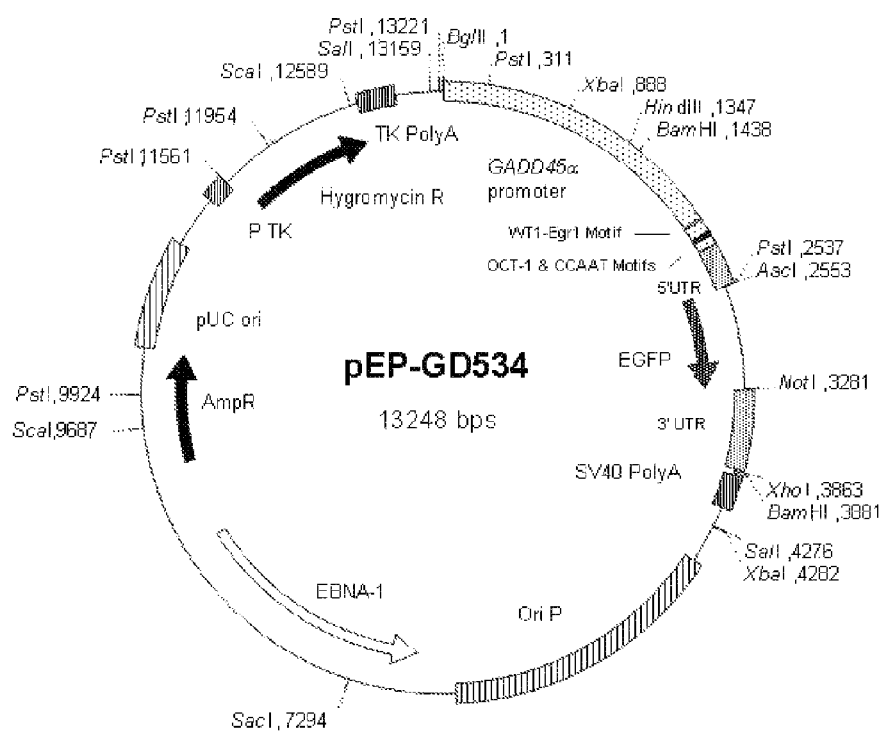
FIG. 8 shows a restriction map of vector pEP-GD534.

These plasmids were named:

(i) pEP-GD531 (3' sequence from +1034 to +3149)—as shown in FIG. 5. This plasmid includes all of Intron 3 of the Human GADD45α gene, including the p53 binding motif;

(ii) pEP-GD532 (3' sequence from +1147 to +3149)—as shown in FIG. 6. This plasmid includes all of Intron 3 of the Human GADD45α gene, including the p53 binding motif;

(iii) pEP-GD533 (3' sequence from +1248 to +3149)—as shown in FIG. 7. This plasmid includes all of Intron 3 of the Human GADD45α gene, including the p53 binding motif; and (iv) pEP-GD534 (3' sequence from +3155 to +3149)—as shown in FIG. 8. This plasmid does not include all of Intron 3 of the Human GADD45α gene, and does not include the p53 binding motif. This plasmid includes the GADD45α 3' untranslated region.

Cloning sites used for step 3:— pEP-GD531: PCR product flanked by Not I (5') and Xho I (3'). Cloned into Not I-Xho I cut pEP-GD500.

pEP-GD532: PCR product flanked by EcoRV (5') and Xho I (3'). Cloned into Hpa I-Xho I cut pEP-GD500.

pEP-GD533: PCR product flanked by Pac I (5') and Xho I (3'). Cloned into Pac I-Xho I cut pEP-GD500.

pEP-GD534: PCR product flanked by Not I (5') and Xho I (3'). Cloned into Not I-Xho I cut pEP-GD500.

Figure 18:
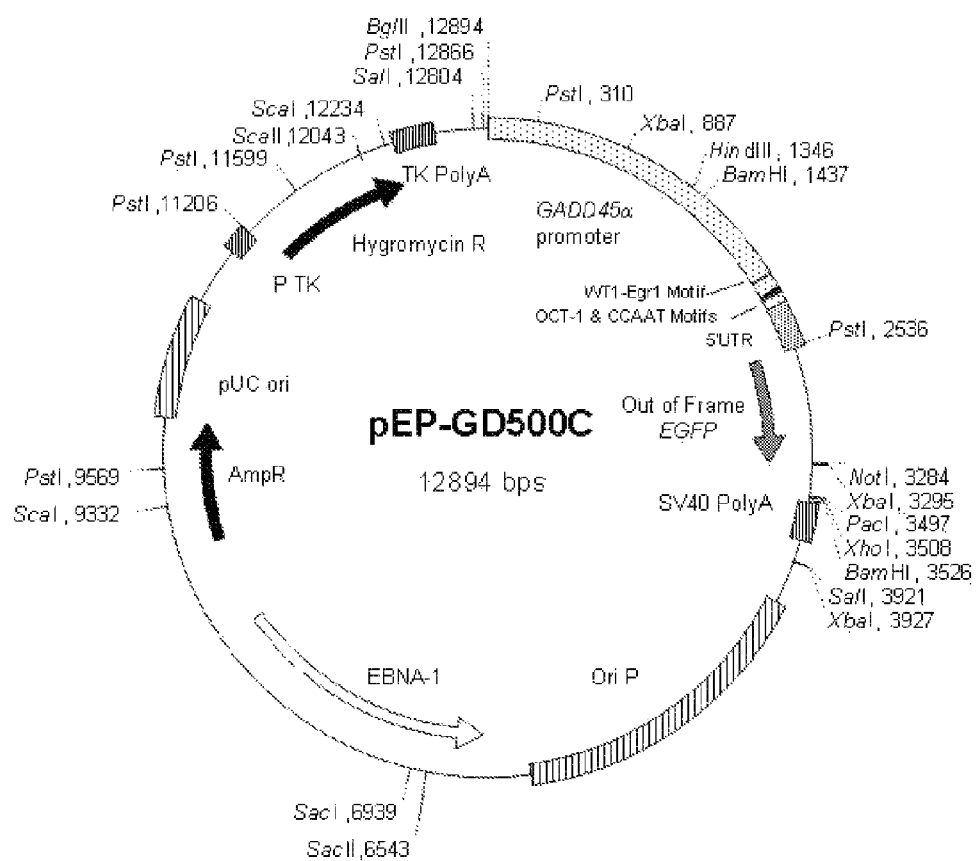
FIG. 18 shows a restriction map of a control vector named pEP-GD500C.
Figure 19:
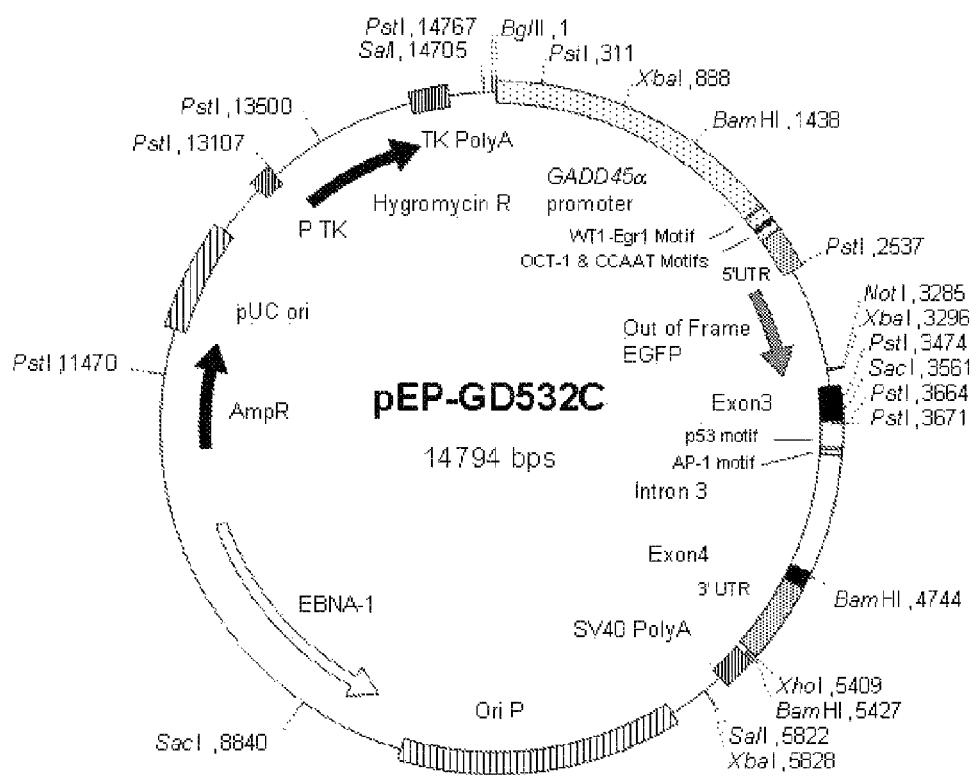
FIG. 19 shows a restriction map of a control vector named pEP-GD532C.

Step 4: (creation of control vectors)—Reporter plasmids were digested with Asc I and the 5' overhangs filled in with Klenow enzyme. The modified DNA fragments were then recirculised. This introduced a 4 bp frameshift in the EGFP gene. The resultant protein is non-functional. The resultant control plasmids are suffixed with the letter C and illustrated in FIGS. 18 and 19.

The DNA sequences of each of the expression cassettes in the plasmids pEP-GD500, pEP-GD531, pEP-GD532, pEP-GD533, and pEP-GD534 are shown in the sequence listing as SEQ ID No.1, SEQ ID No.2, SEQ ID No.3, SEQ ID No.4, and SEQ ID No.5, respectively.

Figure 9:
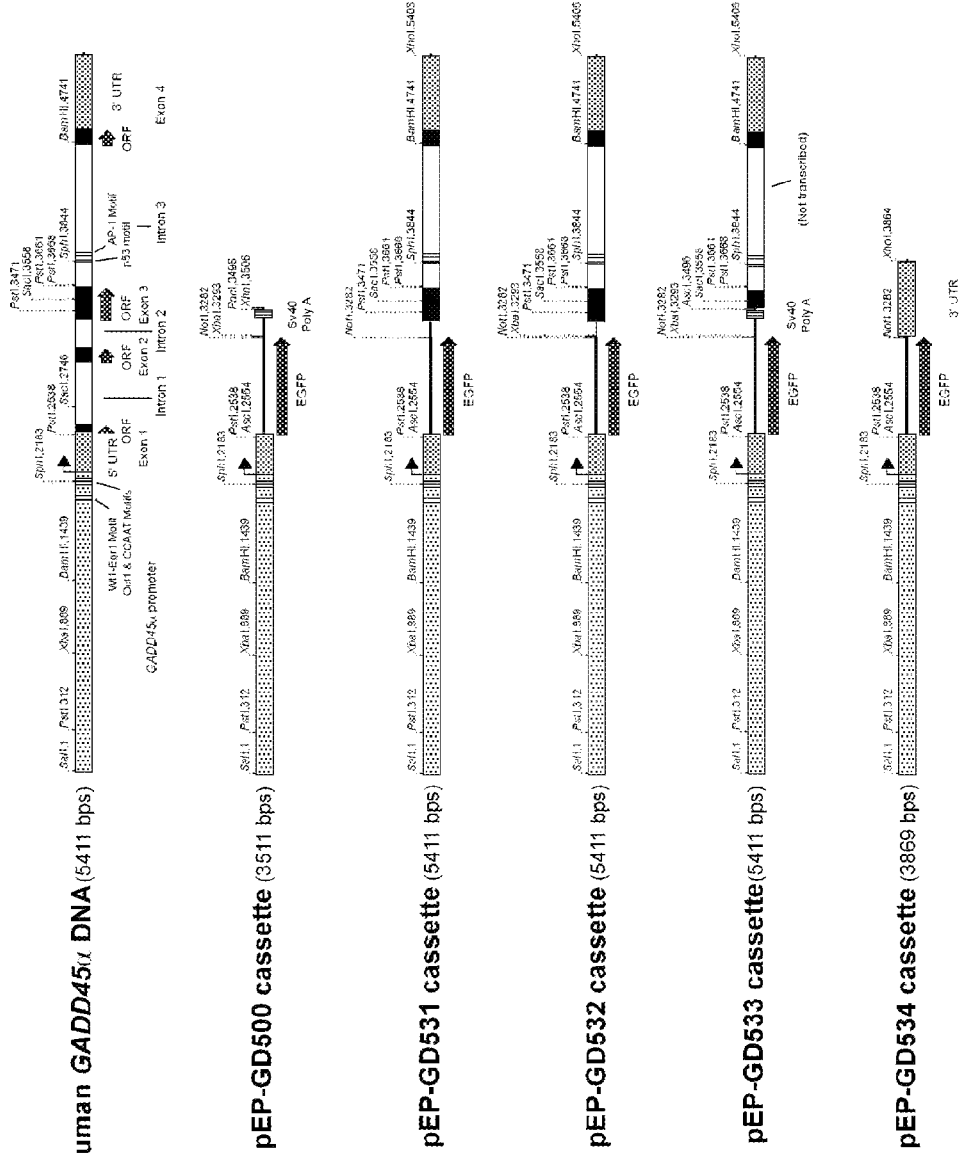
FIG. 9 shows embodiments of reporter expression cassettes according to the invention.

Referring to FIG. 9, there are shown the series of reporter cassettes in accordance with the invention each aligned underneath the Human GADD45α gene. The GADD45α-EGFP reporter gene fusions of plasmids pEP-GD531, pEP-GD532, and pEP-GD533 were constructed in such a way that the overall length of the GADD45α-EGFP fusion is identical to the native GADD45α gene, as shown in FIG. 9. In plasmids pEP-GD531 and pEP-GD532, the GADD45α DNA downstream of the hEGFP is transcribed into mRNA as well as the hEGFP itself, and is subject to splicing. In plasmid pEP-GD533, only the hEGFP gene is transcribed into mRNA. The transcription is stopped at the SV40 polyadenylation signal before the GADD45α gene sequence. These plasmids are in accordance with the first aspect of the invention. The pEP-GD534 cassette is much shorter and does not include the p53 motif in Intron 3 of the GADD45α gene.

1.3 Cell Line Selection and Transfection

When considering a cell line as a host for a new mammalian DNA-damage reporter system, it was important to consider the ability of the chosen cell line to respond to genotoxic damage in a way that would allow the required response of the reporter. The p53 status and effects on downstream genes of two cells lines commonly used in molecular biology and/or genetic toxicology were explored and this work is described herein. These cell lines were:—(i) TK6, a human lymphoblastoid cell line (wt p53); and a sister line of TK6, (ii) WI-L2-NS (mutant p53 protein).

A dysfunctional p53 protein can lead to increased radioresistance (i.e. increased survival) and an increased sensitivity to mutagenic and clastogenic effects of radiation. While these properties make a cell line suitable for detecting mutation endpoints, the same properties imply that the induction of surrogate biomarkers for DNA damage in a cell line with a mutant p53 status would be at best poor. To this end, the TK6 cell line was chosen for the biosensor (i.e. a cell according to the third aspect of the invention). It is believed that additional data of scientific interest may be gained from the use of its sister cell lines with the recombinant GADD45α-EGFP reporter vector.

TK6 cells are transfected with the vectors by electroporation using a method adapted from Xia and Liber [Methods in Molecular biology, Vol. 48: Animal Cell Electroporation and Electrofusion Protocols, 1995. Edited by J. A. Nickoloff. Humana Press Inc., Totowa, N.J., USA, Pages 151-160], and clones bearing the reporter plasmids are selected over two weeks with Hygromycin B.

TK6 cells transformed with pEP-GAD532 are referred to herein as GenTK-T01. An equivalent control cell line, termed GenTK-C01, was also produced in which the GFPreporter gene was deliberately placed out of frame. Accordingly GFP could not be expressed from this control cell line.

1.4 The Assay Media—Modified RPMI

Conventional media may be used in the methods of the invention. However the inventors have found that many traditional cell culture media are autofluorescent at the wavelengths associated with EGFP excitation (488 nm max) and emission (520 nm max). In this work, the major contributing factor of this fluorescence was found to be the vitamin riboflavin. It is therefore preferred that a modified low autofluorescent media is used.

A number of such media may be produced and, by way of example, the inventors developed a modified low autofluorescent RPMI 1640 media (see Table 1). This media represents a preferred media for use according to the fifth aspect of the invention that does not contain any riboflavin, and may be used with the biosensor, to facilitate direct fluorescence reading of biosensor cultures.

TABLE 1 working concentrations of components of a low autofluorescent mammalian cell culture media.

| Component | mg/L |
|---|---|
| INORGANIC SALTS: | |
| Ca(NO$_3$)$_2$•4H$_2$O | 100.00 |
| KCl | 400.00 |
| MgSO$_4$ (anhyd.) | 48.84 |
| NaCl | 6000.00 |

TABLE 1-continued working concentrations of components of a low autofluorescent mammalian cell culture media.

| Component | mg/L |
|---|---|
| NaHCO$_3$ | 2000.00 |
| Na$_2$HPO$_4$ (anhyd.) | 800.00 |
| OTHER COMPONENTS: | |
| D-Glucose | 2000.00 |
| Glutathione (reduced) | 1.00 |
| AMINO ACIDS: | |
| L-Arginine HCl | 241.86 |
| L-Asparagine (free base) | 50.00 |
| L-Aspartic Acid | 20.00 |
| L-Cystine•2HCl | 65.20 |
| L-Glutamic Acid | 20.00 |
| Glycine | 10.00 |
| L-Histidine (free base) | 15.00 |
| L-Hydroxyproline | 20.00 |
| L-Isoleucine | 50.00 |
| L-Leucine | 50.00 |
| L-Lysine•HCl | 40.00 |
| L-Methionine | 15.00 |
| L-Phenylalanine | 15.00 |
| L-Proline | 20.00 |
| L-Serine | 30.00 |
| L-Threonine | 20.00 |
| L-Tryptophan | 5.00 |
| L-Tyrosine (disodium salt) | 28.83 |
| L-Valine | 20.00 |
| VITAMINS: | |
| D-Biotin | 0.20 |
| D-Ca Pantothenate | 0.25 |
| Choline Chloride | 3.00 |
| Folic Acid | 1.00 |
| i-Inositol | 35.00 |
| Nicotinamide | 1.00 |
| Para-aminobenzoic Acid | 1.00 |
| Pyridoxal HCl | 1.00 |
| Thiamine HCl | 1.00 |
| Vitamin B$_{12}$ | 0.005 |

1.5 The Method of Analysis—Microplate Reader

Fluorescence and absorbance data was collected from microplates using the Tecan Ultra-384 (Tecan UK Ltd.) microplate reader: excitation 485 nm/emission 535 nm with an additional dichroic mirror (reflectance 320 nm-500 nm, transmission 520 nm-800 nm). Absorbance was measured through a 620 nm filter. The data were transported into a Microsoft Excel spreadsheet, and converted to graphical data. The absorbance data give an indication of reduction in proliferative potential and these data were normalised to the untreated control (=100% growth). Fluorescence data were divided by absorbance data to give 'brightness units', the measure of average GFP induction per cell. These data were normalised to the untreated control (=1). In this way, one can distinguish between a small number of highly fluorescent cells and a large number of weakly fluorescent cells. In order to correct for induced cellular autofluorescence and intrinsic compound fluorescence, the brightness values for the untransfected TK6 cell line were subtracted from those of the five cell lines bearing a reporter plasmid. This makes visual assessment of the data more reliable. All the data were checked with and without this correction. From this "brightness" data the fluorescence induction ratios were calculated.

1.6 MMS Induction of the Biosensor

As an example of reporter induction, six cell lines (TK6, without a plasmid, and bearing one of the five reporter plasmids) were treated with varying concentrations of MMS. MMS is known to those skilled in the art as a genotoxic and cytotoxic agent and may be used as a positive control when using the method of the invention.

1×10⁶ cells in 1 ml of modified RPMI 1640 media (see 1.4 above)+10% horse Serum were incubated overnight (37° C., 5% $CO_2$, 100% humidity) with 0 μg/ml, 6.25 μg/ml, 12.5 μg/ml, and 25 μg/ml MMS.

After incubation, the cells were washed in PBS, resuspended in 300 μl PBS, and then split into two wells of a well, black, clear-bottomed microplates. For example Matrix ScreenMates, Cat. No. 4929, Apogent Discoveries, USA, or Corning (BV, Netherlands: Cat. No. 3651). Fluorescence and absorbance readings were recorded and fluorescence induction ratios were calculated.

Figure 10:
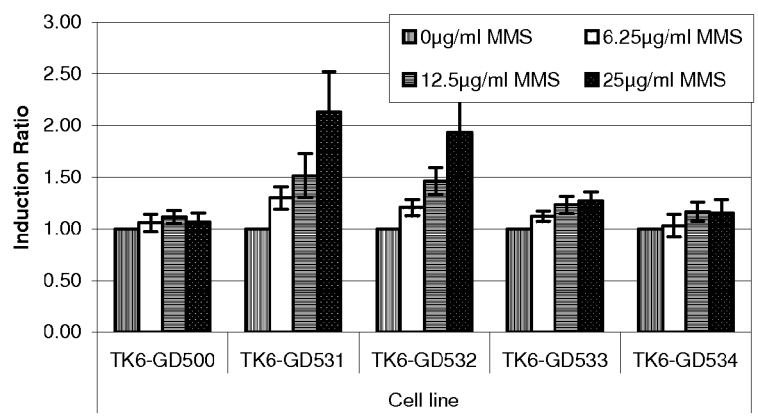
FIG. 10 shows the effect of MMS induction on GADD45α reporter cell lines.

This was repeated three times and the average inductions and standard errors were calculated. The results are illustrated in FIG. 10.

Figure 11:
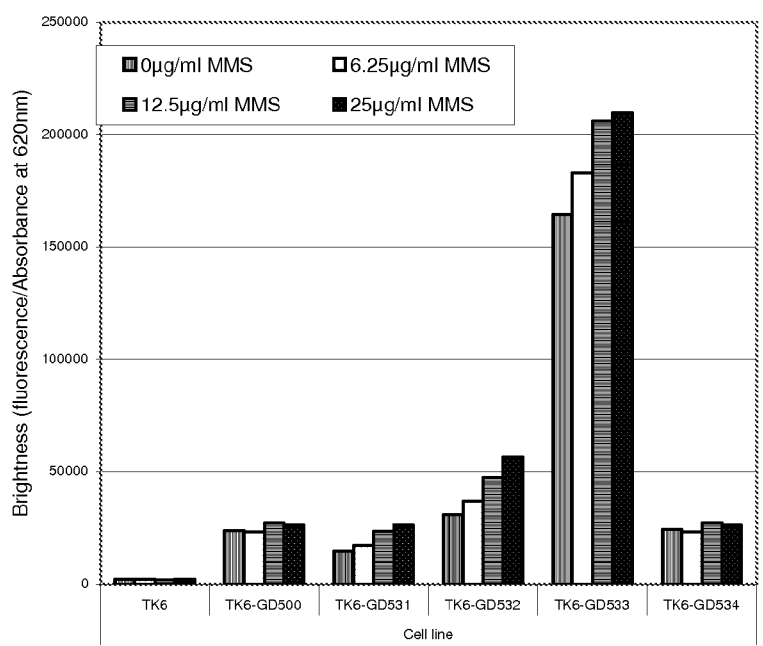
FIG. 11 shows the effect on brightness by MMS induction on GADD45α reporter cell lines.

Referring to FIG. 11, there is shown unprocessed brightness values from the five reporter cell lines and the parent untransfected cell line TK6. Brightness values were calculated for each cell line-MMS combination by measuring the total GFP fluorescence and then normalising this with absorbance at 620 nm. Hence, it will be appreciated that each of the plasmids pEP-GD531, pEP-GD532, and pEP-GD533 show an increase in background fluorescence as compared to the untransfected parent cell line TK6, and these cell lines showed a substantial degree of dose dependent increase in fluorescence in the human cell line TK6 when treated with MMS. In contrast while the cell lines bearing the plasmid pEP-GD500 or pEP-GD534 show an increase in background fluorescence as compared to TK6, this fluorescence is not further induced by treatment with MMS. While the inventors do not wish to be bound by any hypothesis, they believe that the addition of the GADD45α 3' untranslated region in plasmid pEP-GD534 stabilises the resultant mRNA, leading to a higher background level of fluorescence in cell lines bearing this plasmid as compared to cell lines bearing the plasmid pEP-GD500.

In conclusion, the present invention uses the regulatory sequences of the human DNA-Damage inducible gene GADD45α to control the production of EGFP in the p53 wild-type human lymphoblastiod cell line TK6. The human gene GADD45α stimulates DNA excision repair in vitro and inhibits entry of cells into S phase. The reporters in accordance with the invention not only use the upstream promoter of the GADD45α gene, but also incorporate the gene regulatory elements found within the genomic gene sequence itself. This includes a putative p53 binding site in the third Intron of the GADD45α gene. Surprisingly, the use of these sequences enhances the response of the biosensors to genotoxic stress. This reporter system can be analysed for fluorescence induction after only 24 hours by simply measuring the fluorescence of the test culture. The cells may be subjected to an agent, and the expression of the light emitting reporter protein (GFP) from the cell indicates that the agents cause DNA damage. It is believed that this biosensor has applications in short term pre-regulatory drug screening.

Example 2

Further experiments were conducted to evaluate the effects of autofluorescence caused by conventional media in order that preferred media may be developed for use in the method according to the fourth aspect of the invention.

The constructs, cells and protocols described in Example 1 were used unless indicated to the contrary.

As-well-as riboflavin (see 1.4) the inventors established that a second major contribution factor to cell culture media autofluorescence was phenol red (a pH indicator dye commonly used in culture media). The fluorescence of phenol red also varies with pH. Therefore it is preferred that media used according to the invention is formulated as a modified low autofluorescence medium whereby phenol red or riboflavin, but preferably both phenol red and riboflavin, is omitted (see table 1).

Figure 12:
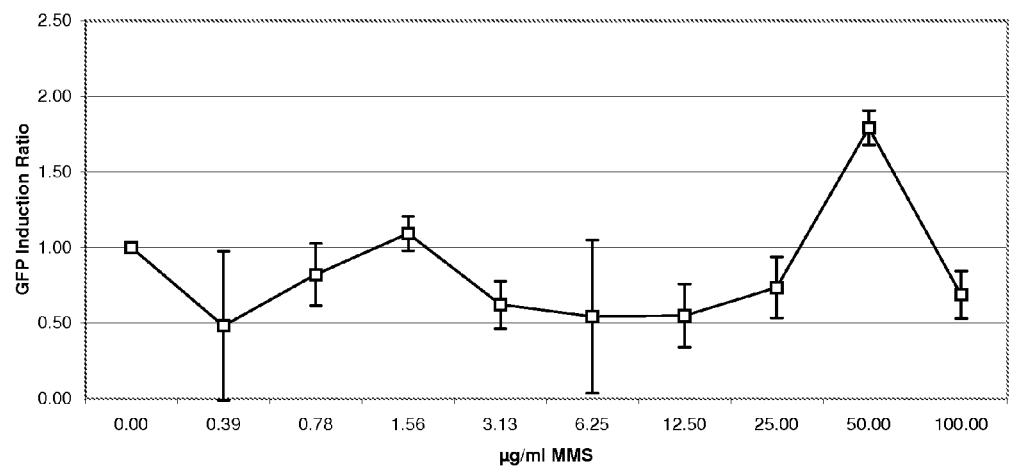
FIG. 12 shows methyl methanesulphonate induced fluorescence measured directly from a reporter cell line cultured in either RPMI 1640 with serum (A) or modified low autofluorescence medium with serum (B) as discussed in Example 2.
Figure 12:
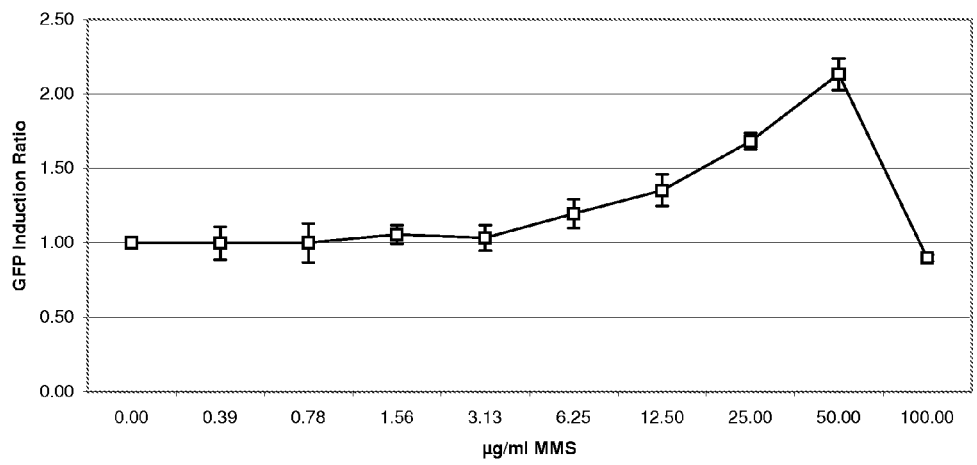

Referring to FIG. 12, the use of conventional RPMI 1640 medium decreased fluorescence signal to noise ratios, and increased variability of fluorescence measurements. Accordingly the use of normal RPMI 1640 media was not optimal for direct fluorescence readings. In contrast, the use of a modified low autofluorescent cell culture media (corresponding to normal media save riboflavain and phenol red was omitted) facilitated the direct measurement of genotoxin induced fluorescence readings.

Figure 13:
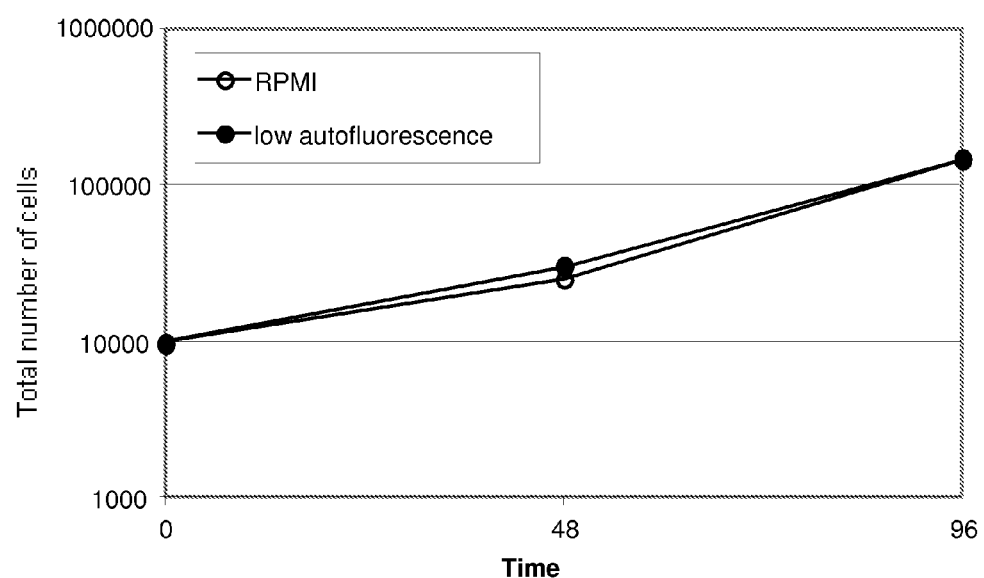
FIG. 13 shows the growth of a human lymphoblastoid cell line in RPMI 1640 or modified low autofluorescence medium in Example 2.

Referring to FIG. 13, the omission of both riboflavin and phenol red from media was found to result in a low autofluorescence medium that did not affect cell growth over 96 hours, and four cell divisions. Accordingly such a media is a preferred media for use according to the fifth aspect of the invention.

It will therefore be appreciated that it is preferred that media used in the method according to the fourth aspect of the invention may comprise conventional media (e.g. RPMI 1640) but is preferably modified, according to the fifth aspect of the invention, such that it does not contain Phenol Red or riboflavin.

Example 3

Further development work was conducted to develop a most preferred protocol for conducting the method according to the fourth aspect of the invention in 96 well plates.

The constructs, cells and protocols described in Example 1 were used unless indicated to the contrary.

A preferred method of testing for DNA damage according to the fourth aspect of the invention comprises the steps of: (1) preparing a microplate for use in an assay; (2) conducting the assay in the microplates; (3) collecting and analysing the data; and (4) making a judgment on DNA damage and the consequences.

Details of steps (1)-(4) for conducting a most preferred test for DNA damage are given below.

3.1 Microplate Preparation.

Assays were carried out in 96 well, black, clear-bottomed microplates. For example Matrix ScreenMates, Cat. No. 4929, Apogent Discoveries, USA, or Corning (BV, Netherlands: Cat. No. 3651). A number of alternative microplates were assessed, though the variable background absorbance and fluorescence both within and between plates from individual manufacturers were found to be variable and in several cases unacceptable. It will therefore be appreciated that microplates used according to the invention preferably have consistent absorbance and fluorescence between plates and batches thereof. It will be appreciated that a skilled person should give careful consideration when selecting a suitable microplate.

The assay plates can be filled using a liquid handling robot. For example the MicroLabS single probe, from Hamilton GB Ltd., Birmingham or a Genesis 8-probe robot (Tecan UK Ltd. Theale. UK). Microplates can also be filled rapidly and effectively using a multi-channel pipette.

3.2 Assay

The following standard protocol may be followed. A 2 mM or 1000 μg/ml (whichever is lowest) stock of a test chemical, or sample containing an agent that putatively caused DNA damage, was prepared in 2% v/v aqueous DMSO, and used to make 2 identical dilution series across a 96 well microplate and a 'control' (see below). To achieve this, 150 microliters of the test chemical solution were put into 2 microplate wells. Each sample was serially diluted by transferring 75 microliters into 75 microliters of 2% DMSO, mixing, and then taking 75 microliters out and into the next well. This produced 9 serial dilutions of 75 microliters each. The final top concentration of test chemical/sample is 1 mM or 500 µg/ml on the microplate.

Controls were added as follows:
a. Test compound/sample containing agent in assay medium alone, to provide information on compound absorbance/fluorescence
b. Human cell cultures diluted with 1% DMSO alone, to give a measure of maximum proliferative potential
c. MMS as a genotoxicity and cytotoxicity control: 'high'=50 µg/ml, 'low'=10 µg/ml v/v
d. 2% DMSO diluent alone, to confirm lack of diluent absorbance/fluorescence
e. Growth medium alone, to confirm sterility/lack of contamination Exponentially growing cultures of cells lines according to the invention (e.g. GenTK-C01 and GenTK-T01) were washed in D-PBS and suspended at a density of $2\times10^6$ cells/ml in double strength low autofluorescent assay medium according to the invention. 75 microliters of the cell suspension were added to each well of the diluted chemical: GenTK-C01 to one series and GenTK-T01 to the second, and to appropriate standards and controls. After the plates were filled, they were sealed using either a gas permeable membrane (for example Breath-easy, Diversified Biotech, USA) or a plastic lid, and then incubated without shaking, for 24 hours at 37° C., 5% $CO_2$, 95% humidity.

3.3 Data Collection and Handling.

Figure 14:
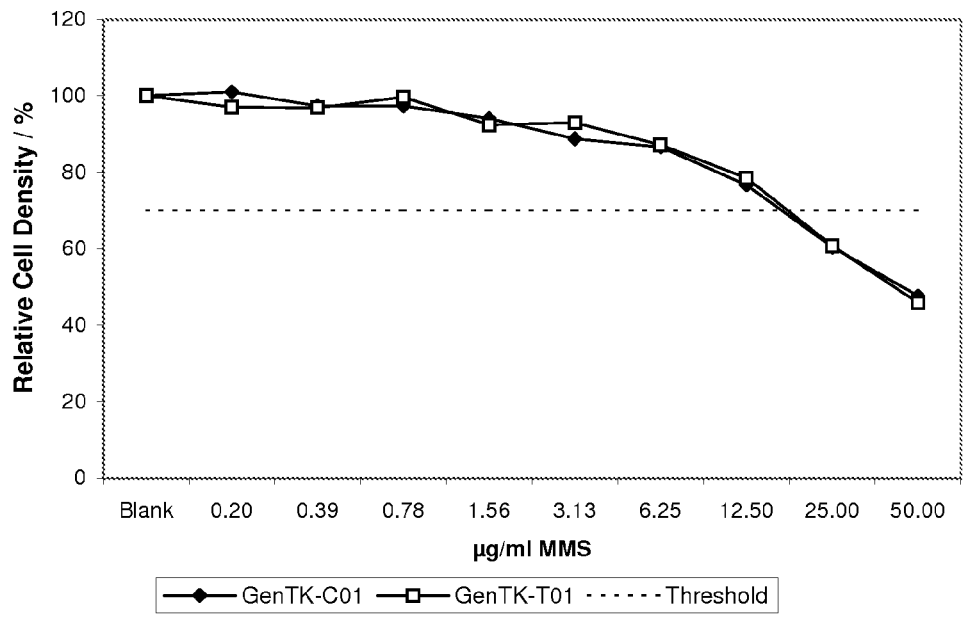
FIG. 14 shows the effect of MMS on relative cell density in a 96 well plate assay after 48 hours incubation in Example 3.
Figure 15:
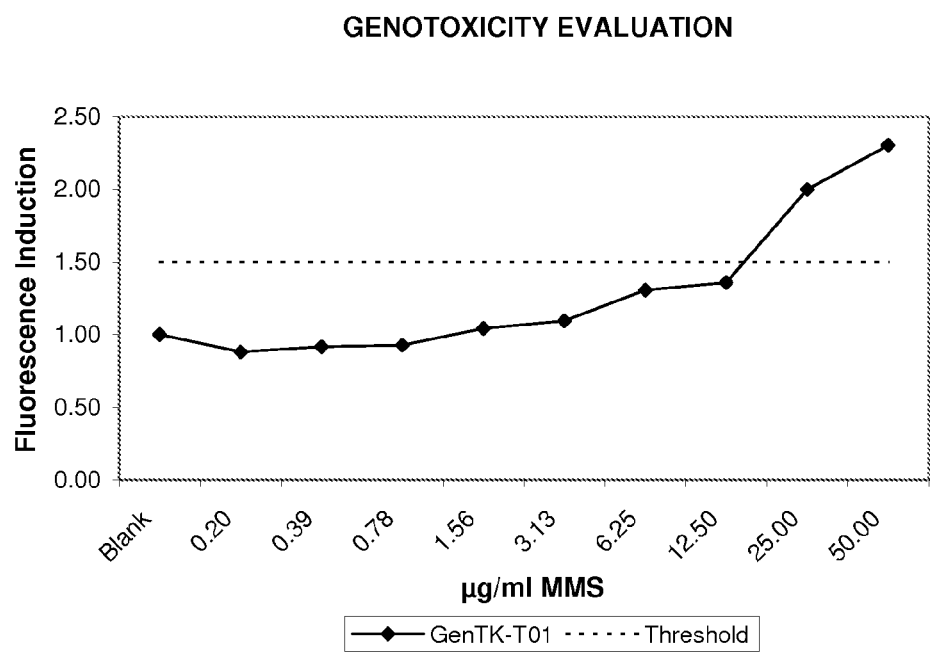
FIG. 15 shows the effect of MMS on florescence induction ratios in a 96 well plate assay in Example 3.

Following 24 hour incubation, fluorescence and absorbance data were collected from the microplates. Two different microplate readers which combine fluorescence and absorbance functionality have been used, and comparable data were obtained. These were a Tecan Ultra-384 (Tecan UK Ltd.): excitation 485 nm/emission 535 nm with an additional dichroic mirror (reflectance 320 nm-500 nm, transmission 520 nm-800 nm), and a Wallac Victor2 (PerkinElmer Life and Analytical Sciences, Monza, Italy): excitation 485 nm/emission 535 nm. Absorbance was measured through a 620 nm filter in both instruments. Microplates were re-sealed using either a gas permeable membrane (for example Breath-easy, Diversified Biotech, USA) or a plastic lid, and then incubated without shaking, for a further 24 hours at 37° C., 5% $CO_2$, 95% humidity. Further absorbance and fluorescence measurements were then collected. The data were transported into a Microsoft Excel spreadsheet, and converted to graphical data (see typical data in FIGS. 14 and 15 for Example 2). Data processing is minimal: absorbance data give an indication of reduction in proliferative potential and these data were normalised to the untreated control (=100% growth). Fluorescence data were divided by absorbance data to give 'brightness units', the measure of average GFP induction per cell. These data were normalised to the untreated control (=1). In this way, one can distinguish between a small number of highly fluorescent cells and a large number of weakly fluorescent cells. In order to correct for induced cellular autofluorescence and intrinsic compound fluorescence, the brightness values for the GenTK-C01 cell line were subtracted from those of GenTK-T01. This makes visual assessment of the data more reliable. All the data were checked with and without this correction, and the decision (see below), on whether or not a compound was classified as being genotoxic, was not affected.

3.4 Decision Thresholds

It is useful to have clear definitions of positive and negative results from routine assays and such definitions have been derived, taking into account the maximum noise in the system and data from chemicals where there is a clear consensus on genotoxicity and mechanism of action. Naturally it is also possible for users to inspect the numerical and graphical data and draw their own conclusions. For example an upward trend in genotoxicity data that did not cross the threshold might still distinguish two compounds. The decision thresholds were set as follows:

The cytotoxicity threshold is set at 80% of the cell density reached by the untreated control cells. This is greater than 3 times the standard deviation of the background. A positive cytotoxicity result (+) is concluded if 1 or 2 compound dilutions produce a final cell density lower than the 80% threshold. A strong positive cytotoxicity result positive (++) is concluded when either (i) three or more compound dilutions produce a final cell density lower than the 80% threshold or (ii) at least one compound dilution produces a final cell density lower than a 60% threshold. A negative result (−) is concluded when no compound dilutions produce a final cell density lower than the 80% threshold. The lowest effective concentration (LEC) is the lowest test compound concentration that produces a final cell density below the 80% threshold.

The compound absorbance control allows a warning to be generated if a test compound is significantly absorbing. If the ratio of the absorbance of the compound control well to a well filled with media alone is >2, there is a risk of interference with interpretation. The cytotoxicity controls indicate that the cell lines are behaving normally. The 'high' MMS standard should reduce the final cell density to below the 80% threshold, and should be a lower value than the 'low' standard.

The genotoxic threshold is set at a relative GFP induction of 1.5 (i.e. a 50% increase). This is greater than 3 times the standard deviation of the background. A positive genotoxicity result (+) is concluded if 1 or 2 compound dilutions produce a relative GFP induction greater than the 1.5 threshold. A strong positive genotoxicity result (++) is concluded if either (i) three or more compound dilutions produce a relative GFP induction greater than the 1.5 threshold or (ii) at least one compound dilution produces a relative GFP induction greater than a 1.8 threshold. A negative genotoxicity result (−) is concluded where no compound dilutions produce a relative GFP induction greater than the 1.5 threshold. The LEC is the lowest test compound concentration that produces a relative GFP induction greater than the 1.5 threshold. The genotoxic controls demonstrate that the cell lines are responding normally to DNA damage. The 'high' MMS standard must produce a fluorescence induction >2, and be a greater value than the 'low' MMS standard. Anomalous brightness data is generated when the toxicity leads to a final cell density less than 30% that of the blank. Genotoxicity data is not calculated above this toxicity threshold. Compounds that tested negative for genotoxicity, were re-tested up to 10 mM or 5000 µg/ml, or to the limit of solubility or cytotoxicity.

The compound fluorescence control allows a warning to be generated when a compound is highly auto-fluorescent. If the ratio of the fluorescence of the compound control well to a media filled well is >5, there is a risk of interference with interpretation. In these cases, fluorescence polarisation can be used to distinguish GFP from other sources of fluorescence (Knight et al., 2000, 2002). The Tecan instrument has this facility. Occasionally, compounds though not fluorescent themselves, induce cellular auto-fluorescence. This is apparent from rising brightness in the control (GenTK-C01) cell line in the absence of fluorescence from the chemical-only control. The routine subtraction of GenTK-C01 from GenTK-T01 data removes this interference from the data.

Example 4

Further development work was conducted to develop another most preferred protocol for conducting the method according to the fourth aspect of the invention in 24 well plates with and without S9 metabolic activation.

S9 is a liver extract (known to the skilled person) that makes it possible to discriminate between genotoxic compounds and some non-genotoxic compounds that may be chemically altered by hepatocyte metabolism to generate a genotoxic compound in vivo.

The constructs, cells and protocols described in Example 1 were used unless indicated to the contrary.

A preferred method of testing for DNA damage according to the fourth aspect of the invention comprises the steps of: (1) preparing a 24 well plate for use in an assay with metabolic activation; (2) conducting the assay in 24 well plates and processing samples in to 96 well plates; (3) collecting and analysing the data; and (4) making a judgment on DNA damage and the consequences.

Details of steps (1)-(4) for conducting a most preferred test for DNA damage are given below.

4.1 Microplate Preparation.

Assays were carried out in 24 well plates (Corning BV, Schiphol-Rijk The Netherlands) and 96 well, black, clear-bottomed microplates. For example Matrix ScreenMates, Cat. No. 4929, Apogent Discoveries, USA, or Corning (BV, Netherlands: Cat. No. 3651). A number of alternative microplates were assessed, though the variable background absorbance and fluorescence both within and between plates from individual manufacturers were generally unacceptable, leading to the currently preferred choice. It will therefore be appreciated that microplates used according to the invention preferably have consistent absorbance and fluorescence between plates and batches thereof.

The assay plates can be filled using a liquid handling robot. For example the MicroLabS single probe, from Hamilton GB Ltd., Birmingham or a Genesis 8-probe robot (Tecan UK Ltd. Theale. UK). Microplates can also be filled rapidly and effectively using a multi-channel pipette.

4.2 Assay

The following standard protocol may be followed. To each row of a 24 well plate 1ml of the following Cell line media combinations were added to each well:
  i) $1\times10^6$ cells/ml GenTK-C01 in RPMI 1640 media
  ii) $1\times10^6$ cells/ml GenTK-T01 in RPMI 1640 media
  iii) $1\times10^6$ cells/ml GenTK-C01 in RPMI 1640 media+10% S9 mix
  iv) $1\times10^6$ cells/ml GenTK-T01 in RPMI 1640 media+10% S9 mix The RPMI 1640 media is preferably a modified media as defined by the fifth aspect of the invention (e.g. the media disclosed in Table 1).

A 100 mg/ml stock of a test chemical, or sample containing an agent that putatively caused DNA damage, was prepared in 100% v/v aqueous DMSO, and used to make 4 identical dilution series across a 24 well microplate and a 'control' (see below). To achieve this, 200 microliters of the test chemical solution were put into a sterile 7 ml glass vial or 1.5 ml microfuge tube. Each sample was serially diluted by transferring 100 microliters into 100 microliters of 100% DMSO, mixing, and then taking 100 microliters out and into the next well. This produced 3 serial dilutions of 100 microliters each. To each well of a 24 well plate The final top concentration of test chemical/sample is 1 mg/ml on the 24 well plate.

Controls were added as follows:
  a. Human cell cultures diluted with 10 μl 100% DMSO alone, to give a measure of maximum proliferative potential
  b. Cyclophosphamide as a positive genotoxicity and cytotoxicity control at 30 μg/ml in the presence of S9.

After the plates were filled, they were sealed using either a gas permeable membrane (for example Breath-easy, Diversified Biotech, USA) or a plastic lid, and then incubated without shaking, for 24 hours at 37° C., 5% $CO_2$, 95% humidity. Following 24 hours incubation cells were transferred to 1.5 ml microfuge tubes and collected by centrifugation at 2500 rcf for 5 minutes. Cells were washed in 500 μl pre-warmed D-PBS (Sigma-Aldrich, Gillingham, UK) and collected by centrifugation as before. Cells were resuspended in 150 μl D-PBS, and cell suspensions transferred to a well of an optically clear bottom, black polystyrene 96 well microplate (Matrix Technologies, Wilmslow, UK). As blanks, 150 μl of D-PBS were added to 2 wells.

4.3 Data Collection and Handling

Figure 16:
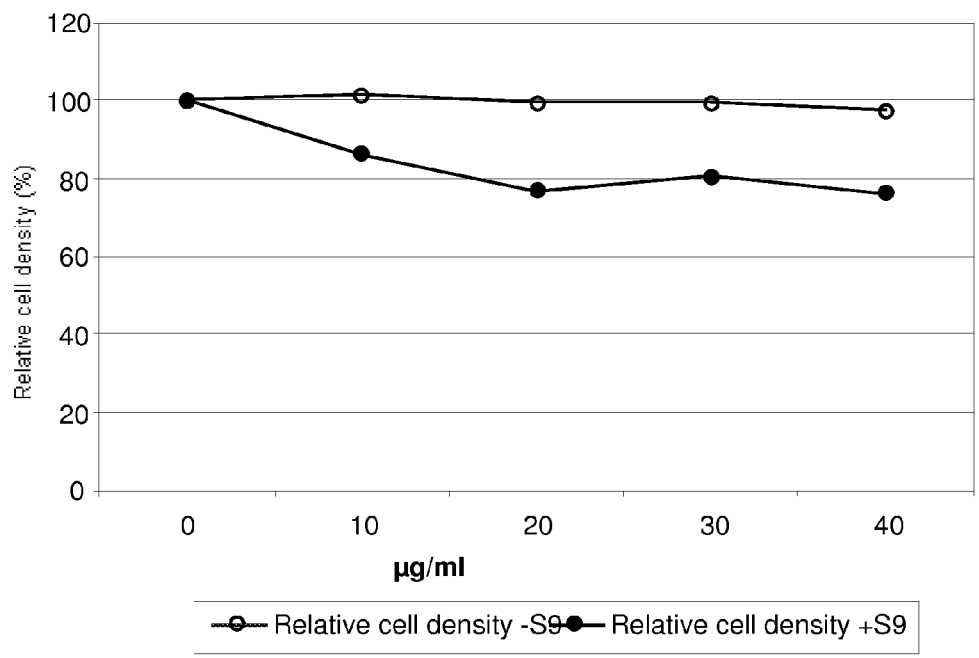
FIG. 16 shows the effect of Cyclophosphamide with and without S9 on the relative cell densitys of GenTK-C01 cells in Example 4.
Figure 17:
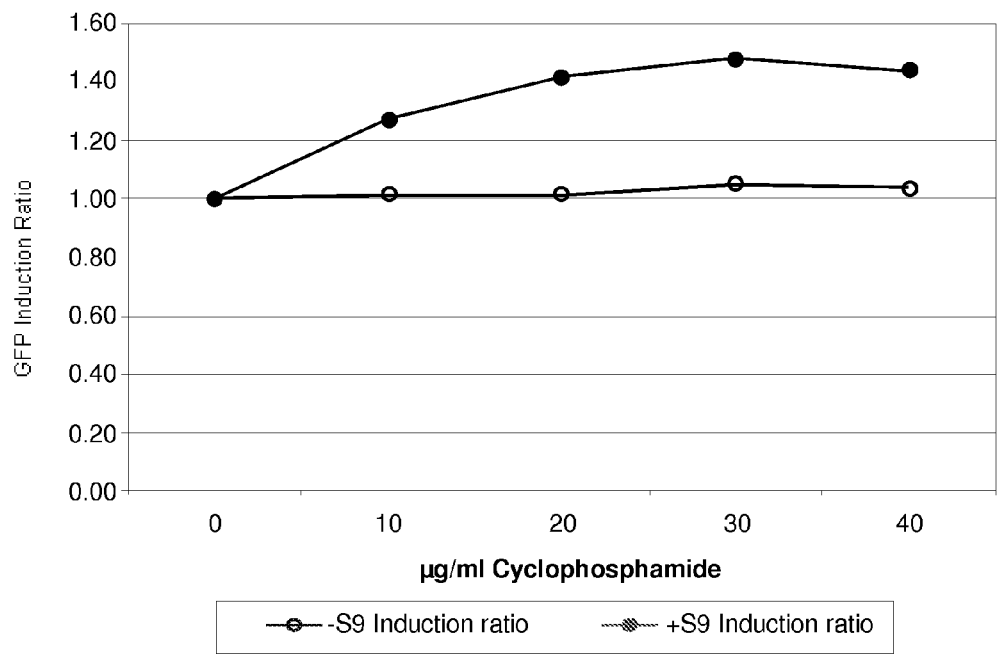
FIG. 17 shows the effect of Cyclophosphamide with and without S9 on the fluorescence induction in GenTK-C01 cells in Example 4.

After transferring cell suspensions to 96 well plates fluorescence and absorbance data were collected. Two different microplate readers which combine fluorescence and absorbance functionality have been used, and comparable data were obtained. These were a Tecan Ultra-384 (Tecan UK Ltd.): excitation 485 nm/emission 535 nm with an additional dichroic mirror (reflectance 320 nm-500 nm, transmission 520 nm-800 nm), and a Wallac Victor2 (PerkinElmer Life and Analytical Sciences, Monza, Italy): excitation 485 nm/emission 535 nm. Absorbance was measured through a 620 nm filter in both instruments. The data were transported into a Microsoft Excel spreadsheet, and converted to graphical data (see typical data in FIGS. 16 and 17 for Example 3). Data processing is minimal: absorbance data give an indication of reduction in proliferative potential and these data were normalised to the untreated control (=100% growth). Fluorescence data were divided by absorbance data to give 'brightness units', the measure of average GFP induction per cell. These data were normalised to the untreated control (=1). In this way, one can distinguish between a small number of highly fluorescent cells and a large number of weakly fluorescent cells. In order to correct for induced cellular autofluorescence and intrinsic compound fluorescence, the brightness values for the GenTK-C01 cell line were subtracted from those of GenTK-T01. This makes visual assessment of the data more reliable. All the data were checked with and without this correction, and the decision (see below), on whether or not a compound was classified as being genotoxic, was not affected.

4.4 Decision Thresholds.

It is useful to have clear definitions of positive and negative results from routine assays and such definitions have been derived, taking into account the maximum noise in the system and data from chemicals where there is a clear consensus on genotoxicity and mechanism of action. Naturally it is also possible for users to inspect the numerical and graphical data and draw their own conclusions. For example an upward trend in genotoxicity data that did not cross the threshold might still distinguish two compounds. The decision thresholds were set as follows:

The cytotoxicity threshold is set at 80% of the cell density reached by the untreated control cells. This is greater than 3 times the standard deviation of the background. A positive cytotoxicity result (+) is concluded if 1 or 2 compound dilutions produce a final cell density lower than the 80% threshold. A strong positive cytotoxicity result positive (++) is concluded when either (i) three or more compound dilutions produce a final cell density lower than the 80% threshold or (ii) at least one compound dilution produces a final cell density lower than a 60% threshold. A negative result (−) is concluded when no compound dilutions produce a final cell density lower than the 80% threshold. The lowest effective concentration (LEC) is the lowest test compound concentration that produces a final cell density below the 80% threshold.

The compound absorbance control allows a warning to be generated if a test compound is significantly absorbing. If the ratio of the absorbance of the compound control well to a well filled with media alone is >2, there is a risk of interference with interpretation. The cytotoxicity controls indicate that the cell lines are behaving normally.

The genotoxic threshold is set at a relative GFP induction of 1.3 (i.e. a 30% increase). This is greater than 3 times the standard deviation of the background. A positive genotoxicity result (+) is concluded if 1 or 2 compound dilutions produce a relative GFP induction greater than the 1.3 threshold. A strong positive genotoxicity result (++) is concluded if either (i) three or more compound dilutions produce a relative GFP induction greater than the 1.3 threshold or (ii) at least one compound dilution produces a relative GFP induction greater than a 1.6 threshold. A negative genotoxicity result (−) is concluded where no compound dilutions produce a relative GFP induction greater than the 1.3 threshold. The LEC is the lowest test compound concentration that produces a relative GFP induction greater than the 1.3 threshold. The genotoxic controls demonstrate that the cell lines are responding normally to DNA damage. The Cyclophosphomide standard must produce a fluorescence induction >1.3 with S9, and not produce a fluorescence induction >1.1 without S9. Anomalous brightness data is generated when the toxicity leads to a final cell density less than 30% that of the blank. Genotoxicity data is not calculated above this toxicity threshold. Compounds that tested negative for genotoxicity, were re-tested up to 10 mM or 5000 μg/ml, or to the limit of solubility or cytotoxicity.

The invention claimed is:

1. A method of detecting for the presence of an agent that causes or potentiates DNA damage comprising subjecting cells to an agent, wherein the cells comprise an expression cassette comprising from 5' to 3', a human GADD45α gene promoter, a DNA sequence encoding a reporter protein, and a human GADD45α gene regulatory element comprising a region of Intron 3 of the GADD45α gene that includes a putative p53 binding motif, wherein the DNA sequence encoding the reporter protein is expressed in response to DNA damage caused by the agent; and monitoring the expression of the reporter protein from the cell, wherein a threshold increase in expression of the DNA sequence encoding the reporter protein relative to a control indicates that the agent causes or potentiates DNA damage.

2. The method according to claim 1, wherein the agent is further screened to assess whether it is safe to expose a living organism to the agent.

3. The method according to claim 1, wherein the agent is a candidate medicament, food additive or cosmetic.

4. The method according to claim 1, wherein the expression of a light emitting reporter protein from the cells is monitored.

5. The method according to claim 4, wherein the light emitting reporter protein is Green Fluorescent Protein.

6. The method according to claim 5, comprising growing the cells, incubating the cells with the agent for a pre-determined time, and monitoring the expression of the Green Fluorescent Protein directly from a sample of the cells.

7. The method according to claim 1, wherein the cells are grown in a low fluorescence growth medium.

8. The method according to claim 7, wherein the low fluorescence growth medium is an RPMI medium containing no riboflavin.

9. The method according to claim 7, wherein the low fluorescence growth medium is an RPMI medium containing no phenol red.

10. The method according to claim 4, wherein fluorescence is determined by comparing fluorescence from the cells with fluorescence from a control cell comprising a vector in which a nucleic acid encoding a light emitting reporter protein is out of frame.

* * * * *

SEQUENCE LISTING

```
<160> NUMBER OF SEQ ID NOS: 5

<210> SEQ ID NO 1
<211> LENGTH: 3516
<212> TYPE: DNA
<213> ORGANISM: Homo sapiens
<220> FEATURE:
<221> NAME/KEY: GADD45 alpha promoter
<222> LOCATION: (4)..(2254)
<223> OTHER INFORMATION:
<220> FEATURE:
<221> NAME/KEY: GADD45 alpha 5' UTR
<222> LOCATION: (2255)..(2549)
<223> OTHER INFORMATION:
<220> FEATURE:
<221> NAME/KEY: EGFP gene
<222> LOCATION: (2550)..(3278)
<223> OTHER INFORMATION:
<220> FEATURE:
<221> NAME/KEY: SV40 polyA
<222> LOCATION: (3432)..(3482)
<223> OTHER INFORMATION:

<400> SEQUENCE: 1
atcagatctt gggtggggca ctttaggact gtggttcatt tgaattggtg taaacaatac      60
accggttcta ctgtcctaca gcctccattc agatgactga agtcatggga ctttcagcat     120
agctagctga tgacagtgca tactattttg tcccaaaatc cagttcaagc atggacatac     180
caataagagc ctaagctctt taaaggcaaa ggaccaggaa ttgtacagtt cttggtatag     240
aagaagacag gcaaaagtgt ttttgaacta acgttaaatg tgcaatatgt tagaattcat     300
gcaatgcaca ggactgcagg attctgatat cttatttaac tctcaaattc tattcaactc     360
aataaacctt gactgtgctt ctactaaatg caggtattgt actaggagct gaggacacca     420
aactgatgaa gtccttgctg tcaagaaact cacatgattc cctaattctt tgtcagcttg     480
ctgtgatcac attttcttcc caagaacctc taagaaatgc ctagtggata gaaccttgga     540
gttccacgga acatattaac aatcgccaaa tgatgactca ggctagattg tgtaattcag     600
gttttgtctg caaaactgaa aatgcttcgg taacctacct aaatttcaat gttgaggaat     660
tctttaagaa agacatcaaa tgttaagatt taaggcatag atatgagata catagtcatg     720
cttaggtgaa ttatgcactg accatgacca tttctttact caaatgttgt ccatggctga     780
```

```
caacacagtg aaaaaatgag tgcaaaatga caactcaaat aaatgaacca gaaaacctat      840
cacttttctt ttccaccaaa ttaagatcaa gagagctgga gaatattttg tctagagtga      900
taaaaacata agggtgcaaa acttccaggt acctttgcag aaattacttc tgtgacctt       960 ggctgtacag caaccttaat aatgcaagca ctgttttgaa tgcaagcatg tgggagccat     1020
tttcaccact tttgatgact tcagtaggtt taagaaatgt ttttgctttt attgcataaa     1080
ccataaaaca aaggaaggga cttttgaact actcagtgag agtctatata ttaaagtttg     1140
tttttcaaaa atgtgtaact accatttgca gttttaaagg tctgctttcc acctacaagt     1200
tgccattatc tcaaaggtga aattttagca tatgactaaa aacttcctat agttacagct     1260
tcatgattca gcatctaaca tcaataattc acagtgagat cataggaggc tctctgtgga     1320
aggtaacgac atacatacgt taggaaagga agcttagggc atatcgagag cattttgaat     1380
ttagacttgt gggctgtgtg ggtgtcagat ggttgtctct cagctggtgg gcgtccagaa     1440
ggatccttgt tgggcaagg ctcttttgaga aaggagaatc tggggttgcca gggattccca     1500 catgtggtca ccagctcccc acgcagacca gctcacgatt tcccagttac accgggcagg     1560
tgggaaaccg ttctgctttc tgtggaaaag attctaactt ggttccctgc atccctgaa      1620 tacaaacggg ttggtttttc ttttttcagc ttccaaccct tgcagctttc caaaaataaa     1680
tcaaaccagc catcagggca ccgaaataat actactgcta ataagcagct tcgcctagac     1740
ttagataaac aacacttctg aggtaaactt tgccccggag gtctggagac acttttttaa     1800
tgtaacctgc ttactaataa ttactagact tcagtgcatt aaccctggaa atagatttta     1860
atagccaccc cttaaaacaa aagacatgaa aagataataa gaaaaaagtg ccgcaactat     1920
tatagaaaaa cacttggcag cctgcttcag cccaagctga ggccacctct agcctctgct     1980 aaagccccc actcccaatg gtccccgcca accggataag agtgcgcgcg ggacccgcct     2040 tccctctcg gcaccgcccc cgcccccgcc ccctcggctc gcctcccgcg tggctcctcc     2100
cttttccgct cctctcaacc tgactccagg agctggggtc aaattgctgg agcaggctga     2160
tttgcatagc ccaatggcca agctgcatgc aaatgaggcg gaaggtggtt ggctgagggt     2220
tggcaggata accccggaga gcggggccct ttgtcctcca gtggctggta ggcagtggct     2280
gggaggcagc ggcccaatta gtgtcgtgcg gcccgtggcg aggcgaggtc cggggagcga     2340
gcgagcaagc aaggcgggag gggtggccgg agctgcggcg gctggcacag gaggaggagc     2400
ccgggcgggc gaggggcggc cggagagcgc cagggcctga gctgccggag cggcgcctgt     2460
gagtgagtgc agaaagcagg cgcccgcgcg ctagccgtgg caggagcagc ccgcacgccg     2520
cgctctctcc ctgggcgacc tgcagtttgc aatatggcgc gcctggtgag caagggcgag     2580
gagctgttca ccggggtggt gcccatcctg gtcgagctgg acggcgacgt aaacggccac     2640
aagttcagcg tgtccggcga gggcgagggc gatgccacct acggcaagct gaccctgaag     2700
ttcatctgca ccaccggcaa gctgcccgtg ccctggccca cctcgtgac caccctgacc      2760 tacggcgtgc agtgcttcag ccgctacccc gaccacatga agcagcacga cttcttcaag     2820
tccgccatgc ccgaaggcta cgtccaggag cgcaccatct tcttcaagga cgacggcaac     2880
tacaagaccc gcgccgaggt gaagttcgag ggcgacaccc tggtgaaccg catcgagctg     2940
aagggcatcg acttcaagga ggacggcaac atcctggggc acaagctgga gtacaactac     3000
aacagccaca acgtctatat catggccgac aagcagaaga acggcatcaa ggtgaacttc     3060
aagatccgcc acaacatcga ggacggcagc gtgcagctcg ccgaccacta ccagcagaac     3120
```

```
acccccatcg gcgacggccc cgtgctgctg cccgacaacc actacctgag cacccagtcc    3180
gccctgagca agaccccaa cgagaagcgc gatcacatgg tcctgctgga gttcgtgacc    3240
gccgccggga tcactctcgg catggacgag ctgtacaagt aaagcggccg cgactctaga    3300
tcataatcag ccataccaca tttgtagagg ttttacttgc tttaaaaaac ctcccacacc    3360
tccccctgaa cctgaaacat aaaatgaatg caattgttgt tgttaacttg tttattgcag    3420
cttataatgg ttacaaataa agcaatagca tcacaaattt cacaaataaa gcatttttt    3480 cactgcattc tagttgttaa ttaatgcctc gagcgc                             3516

<210> SEQ ID NO 2
<211> LENGTH: 5411
<212> TYPE: DNA
<213> ORGANISM: Homo sapiens
<220> FEATURE:
<221> NAME/KEY: GADD45alpha promoter
<222> LOCATION: (4)..(2254)
<223> OTHER INFORMATION:
<220> FEATURE:
<221> NAME/KEY: GADD45alpha 5' UTR
<222> LOCATION: (2255)..(2549)
<223> OTHER INFORMATION:
<220> FEATURE:
<221> NAME/KEY: EGFP gene
<222> LOCATION: (2550)..(3278)
<223> OTHER INFORMATION:
<220> FEATURE:
<221> NAME/KEY: GAD45alpha Exon 3
<222> LOCATION: (3405)..(3642)
<223> OTHER INFORMATION:
<220> FEATURE:
<221> NAME/KEY: GAD45alpha Intron 3
<222> LOCATION: (3643)..(4715)
<223> OTHER INFORMATION:
<220> FEATURE:
<221> NAME/KEY: p53 motif
<222> LOCATION: (3830)..(3849)
<223> OTHER INFORMATION:
<220> FEATURE:
<221> NAME/KEY: AP-1 motif
<222> LOCATION: (3879)..(3885)
<223> OTHER INFORMATION:
<220> FEATURE:
<221> NAME/KEY: GADD45alpha Exon 4
<222> LOCATION: (4716)..(5391)
<223> OTHER INFORMATION:
<220> FEATURE:
<221> NAME/KEY: GADD45alpha 3' UTR
<222> LOCATION: (4830)..(5391)
<223> OTHER INFORMATION:

<400> SEQUENCE: 2
atcagatctt gggtggggca ctttaggact gtggttcatt tgaattggtg taaacaatac     60
accggttcta ctgtcctaca gcctccattc agatgactga agtcatggga ctttcagcat    120
agctagctga tgacagtgca tactattttg tcccaaaatc cagttcaagc atggacatac    180
caataagagc ctaagctctt taaaggcaaa ggaccaggaa ttgtacagtt cttggtatag    240
aagaagacag gcaaaagtgt ttttgaacta acgttaaatg tgcaatatgt tagaattcat    300
gcaatgcaca ggactgcagg attctgatat cttatttaac tctcaaattc tattcaactc    360
aataaacctt gactgtgctt ctactaaatg caggtattgt actaggagct gaggacacca    420
aactgatgaa gtccttgctg tcaagaaact cacatgattc cctaattctt tgtcagcttg    480
ctgtgatcac atttcttcc caagaacctc taagaaatgc ctagtggata gaaccttgga    540
gttccacgga acatattaac aatcgccaaa tgatgactca ggctagattg tgtaattcag    600
gttttgtctg caaaactgaa aatgcttcgg taacctacct aaatttcaat gttgaggaat    660
```

```
tctttaagaa agacatcaaa tgttaagatt taaggcatag atatgagata catagtcatg      720
cttaggtgaa ttatgcactg accatgacca tttctttact caaatgttgt ccatggctga      780
caacacagtg aaaaaatgag tgcaaaatga caactcaaat aaatgaacca gaaaacctat      840
cacttttctt ttccaccaaa ttaagatcaa gagagctgga gaatattttg tctagagtga      900
taaaaacata agggtgcaaa acttccaggt acctttgcag aaattacttc tgtgacccttt     960 ggctgtacag caaccttaat aatgcaagca ctgttttgaa tgcaagcatg tgggagccat     1020
tttcaccact tttgatgact tcagtaggtt taagaaatgt ttttgctttt attgcataaa     1080
ccataaaaca aaggaaggga cttttgaact actcagtgag agtctatata ttaaagtttg     1140
tttttcaaaa atgtgtaact accatttgca gttttaaagg tctgctttcc acctacaagt     1200
tgccattatc tcaaaggtga aattttagca tatgactaaa aacttcctat agttacagct     1260
tcatgattca gcatctaaca tcaataattc acagtgagat cataggaggc tctctgtgga     1320
aggtaacgac atacatacgt taggaaagga agcttagggc atatcgagag cattttgaat     1380
ttagacttgt gggctgtgtg ggtgtcagat ggttgtctct cagctggtgg gcgtccagaa     1440
ggatccttgt ttgggcaagg ctctttgaga aaggagaatc tgggttgcca gggattccca     1500
catgtggtca ccagctcccc acgcagacca gctcacgatt tcccagttac accgggcagg     1560
tgggaaaccg ttctgctttc tgtggaaaag attctaactt ggttccctgc catccctgaa     1620
tacaaacggg ttggttttc tttttcagc ttccaaccct tgcagctttc caaaaataaa       1680
tcaaaccagc catcagggca ccgaaataat actactgcta ataagcagct tcgcctagac     1740
ttagataaac aacacttctg aggtaaactt tgccccggag gtctggagac actttttttaa    1800 tgtaacctgc ttactaataa ttactagact tcagtgcatt aaccctggaa atagatttta     1860
atagccaccc cttaaaacaa aagacatgaa aagataataa gaaaaaagtg ccgcaactat     1920
tatagaaaaa cacttggcag cctgcttcag cccaagctga ggccacctct agcctctgct     1980
aaagcccccc actcccaatg gtccccgcca accggataag agtgcgcgcg ggacccgcct     2040 tccccctctcg gcaccgcccc cgcccccgcc ccctcggctc gcctcccgcg tggctcctcc    2100
cttttccgct cctctcaacc tgactccagg agctggggtc aaattgctgg agcaggctga     2160
tttgcatagc ccaatggcca agctgcatgc aaatgaggcg gaaggtggtt ggctgagggt     2220
tggcaggata accccggaga gcggggcct ttgtcctcca gtggctggta ggcagtggct      2280
gggaggcagc ggcccaatta gtgtcgtgcg gcccgtggcg aggcgaggtc cggggagcga     2340
gcgagcaagc aaggcgggag gggtggccgg agctgcggcg gctggcacag gaggaggagc     2400
ccgggcgggc gaggggcggc cggagagcgc cagggcctga gctgccggag cggcgcctgt     2460
gagtgagtgc agaaagcagg cgcccgcgcg ctagccgtgg caggagcagc ccgcacgccg     2520
cgctctctcc ctgggcgacc tgcagtttgc aatatggcgc gcctggtgag caagggcgag     2580
gagctgttca ccggggtggt gcccatcctg gtcgagctgg acggcgacgt aaacggccac     2640
aagttcagcg tgtccggcga gggcgagggc gatgccacct acggcaagct gaccctgaag     2700
ttcatctgca ccaccggcaa gctgcccgtg ccctggccca ccctcgtgac caccctgacc     2760
tacggcgtgc agtgcttcag ccgctacccc gaccacatga agcagcacga cttcttcaag     2820
tccgccatgc ccgaaggcta cgtccaggag cgcaccatct tcttcaagga cgacggcaac     2880
tacaagaccc gcgccgaggt gaagttcgag ggcgacaccc tggtgaaccg catcgagctg     2940
aagggcatcg acttcaagga ggacggcaac atcctggggc acaagctgga gtacaactac     3000
```

```
aacagccaca acgtctatat catggccgac aagcagaaga acggcatcaa ggtgaacttc    3060
aagatccgcc acaacatcga ggacggcagc gtgcagctcg ccgaccacta ccagcagaac    3120
accccccatcg gcgacggccc cgtgctgctg cccgacaacc actacctgag cacccagtcc    3180
gccctgagca agacccccaa cgagaagcgc gatcacatgg tcctgctgga gttcgtgacc    3240
gccgccggga tcactctcgg catggacgag ctgtacaagt aaagcggccg cttctgcctg    3300
tctcggaagg gaggggggcga gcgggccggg cggcgacccc cagggacccg ggcagtggtt    3360
gagggcgccc gcgcttctgc gctcactggc cccgcccgct gccccagcg accccgataa    3420
cgtggtgttg tgcctgctgg cggcggacga ggacgacgac agagatgtgg ctctgcagat    3480
ccacttcacc ctgatccagg cgttttgctg cgagaacgac atcaacatcc tgcgcgtcag    3540
caacccgggc cggctggcgg agctcctgct cttggagacc gacgctggcc ccgcggcgag    3600
cgagggcgcc gagcagcccc cggacctgca ctgcgtgctg gtgacggtaa gggactgggg    3660
gactgcagcc tgcagggtag agccccggaa ggacgggagt cagggctggg ttgcctgatt    3720
gtggatctgt ggtaggtggg ggtcaggagg gtggctgcct ttgtccgact agagtgtggc    3780
tggactttca gccgagatgt gctagtttca tcaccaggat tttctgtggt acagaacatg    3840
tctaagcatg ctggggactg ccagcagcgg aagagatccc tgtgagtcag cagtcagccc    3900
agctactccc tacctacatc tgcactgcct cccgtgacta attcctttag cagggcagat    3960
tagataaagc caaatgaatt cctggctcac ccctcattaa ggagtcagct tcattctctg    4020
ccagtcagag ctaaaaatag aaattgtgta ggagacaaac cttgttaatt ccctagaaat    4080
acattaagag gatagagtgg aatttttttt ctctgcaatc ttgcattttt ttaatggctc    4140
tttttttttt tcctgataaa aacctttggt aggtagggaa gttatgtttt caggggtaaa    4200
tgtgctactt ttgtcttcta aatttgctc ttttttgact ggtctagtca agtgacagcc    4260
cgattatttt gctactcctt aaaagtacta ttctgtctct tggagtatgg ttgatggcaa    4320
ttccagttaa ctgctgtgca gctctcatct cattgtgcac acagcatgga aatctttctc    4380
aaaactgttt cactcaggtc agggtaacaa gtttggtaga gcaaaccggt gaatgatact    4440
ctcatgcaaa actgaacaga tatgcaaaca tatgtatgtg gttcagcttg ggttgcatgg    4500
gttcagactt tgcaatgtgt agtttaatag gtaattaccc ttaacgcttt tgcagggaac    4560
ccaactacct tgaagaaact ttaatttttt tgtgcttcta atttgtctcc atgtcacata    4620
gccaaaatat agaatgttca agtgttttct cctcaaaagt ataattacta gaatatactg    4680
gttttttaaaa taagtttatt tttataaatt tgtttccaga atccacattc atctcaatgg    4740
aaggatcctg ccttaagtca acttatttgt ttttgccggg aaagtcgcta catggatcaa    4800
tgggttccag tgattaatct ccctgaacgg tgatggcatc tgaatgaaaa taactgaacc    4860
aaattgcact gaagttttg aaatacccttt gtagttactc aagcagttac tccctacact    4920
gatgcaagga ttacagaaac tgatgccaag gggctgagtg agttcaacta catgttctgg    4980
gggcccggag atagatgact ttgcagatgg aaagaggtga aatgaagaa ggaagctgtg    5040
ttgaaacaga aaataagtc aaaaggaaca aaaattacaa agaaccatgc aggaaggaaa    5100
actatgtatt aatttagaat ggttgagtta cattaaaata aaccaaatat gttaaagttt    5160
aagtgtgcag ccatagtttg ggtattttg gtttatatgc cctcaagtaa aagaaaagcc    5220
gaaagggtta atcatatttg aaaaccatat tttattgtat tttgatgaga tattaaattc    5280
tcaaagttt attataaatt ctactaagtt attttatgac atgaaaagtt atttatgcta    5340
taaatttttt gaaacacaat acctacaata aactggtatg aataattgca tcatttctta    5400
```

```
ttgtgtgctc g                                                        5411
```

<210> SEQ ID NO 3
<211> LENGTH: 5411
<212> TYPE: DNA
<213> ORGANISM: Homo sapiens
<220> FEATURE:
<221> NAME/KEY: GADD45alpha promoter
<222> LOCATION: (4)..(2254)
<223> OTHER INFORMATION:
<220> FEATURE:
<221> NAME/KEY: GADD45alpha 5' UTR
<222> LOCATION: (2255)..(2549)
<223> OTHER INFORMATION:
<220> FEATURE:
<221> NAME/KEY: EGFP gene
<222> LOCATION: (2550)..(3278)
<223> OTHER INFORMATION:
<220> FEATURE:
<221> NAME/KEY: GADD45alpha Exon 3
<222> LOCATION: (3405)..(3642)
<223> OTHER INFORMATION:
<220> FEATURE:
<221> NAME/KEY: GADD45alpha Intron 3
<222> LOCATION: (3643)..(4715)
<223> OTHER INFORMATION:
<220> FEATURE:
<221> NAME/KEY: p53 motif
<222> LOCATION: (3830)..(3849)
<223> OTHER INFORMATION:
<220> FEATURE:
<221> NAME/KEY: GADD45alpha Exon 4
<222> LOCATION: (4716)..(5391)
<223> OTHER INFORMATION:
<220> FEATURE:
<221> NAME/KEY: GADD45alpha 3' UTR
<222> LOCATION: (4830)..(5391)
<223> OTHER INFORMATION:

<400> SEQUENCE: 3

```
atcagatctt gggtggggca ctttaggact gtggttcatt tgaattggtg taaacaatac    60
accggttcta ctgtcctaca gcctccattc agatgactga agtcatggga ctttcagcat   120
agctagctga tgacagtgca tactattttg tcccaaaatc cagttcaagc atggacatac   180
caataagagc ctaagctctt taaaggcaaa ggaccaggaa ttgtacagtt cttggtatag   240
aagaagacag gcaaaagtgt ttttgaacta acgttaaatg tgcaatatgt tagaattcat   300
gcaatgcaca ggactgcagg attctgtatat cttatttaac tctcaaattc tattcaactc   360
aataaacctt gactgtgctt ctactaaatg caggtattgt actaggagct gaggacacca   420
aactgatgaa gtccttgctg tcaagaaact cacatgattc cctaattctt tgtcagcttg   480
ctgtgatcac attttcttcc caagaacctc taagaaatgc ctagtggata gaaccttgga   540
gttccacgga acatattaac aatcgccaaa tgatgactca ggctagattg tgtaattcag   600
gttttgtctg caaaactgaa aatgcttcgg taacctacct aaatttcaat gttgaggaat   660
tctttaagaa agacatcaaa tgttaagatt taaggcatag atatgagata catagtcatg   720
cttaggtgaa ttatgcactg accatgacca tttctttact caaatgttgt ccatggctga   780
caacacagtg aaaaaatgag tgcaaaatga caactcaaat aaatgaacca gaaaaccctat   840
cactttctt ttccaccaaa ttaagatcaa gagagctgga gaatatttg tctagagtga   900
taaaaacata agggtgcaaa acttccaggt acctttgcag aaattacttc tgtgaccttt   960
ggctgtacag caaccttaat aatgcaagca ctgtttgaa tgcaagcatg tgggagccat  1020
tttcaccact tttgatgact tcagtaggtt taagaaatgt ttttgctttt attgcataaa  1080
```

```
ccataaaaca aaggaaggga cttttgaact actcagtgag agtctatata ttaaagtttg    1140
tttttcaaaa atgtgtaact accatttgca gttttaaagg tctgctttcc acctacaagt    1200
tgccattatc tcaaaggtga aattttagca tatgactaaa aacttcctat agttacagct    1260
tcatgattca gcatctaaca tcaataattc acagtgagat cataggaggc tctctgtgga    1320
aggtaacgac atacatacgt taggaaagga agcttagggc atatcgagag cattttgaat    1380
ttagacttgt gggctgtgtg ggtgtcagat ggttgtctct cagctggtgg gcgtccagaa    1440
ggatccttgt ttgggcaagg ctctttgaga aaggagaatc tgggttgcca gggattccca    1500
catgtggtca ccagctcccc acgcagacca gctcacgatt tcccagttac accgggcagg    1560
tgggaaaccg ttctgctttc tgtggaaaag attctaactt ggttccctgc catccctgaa    1620
tacaaacggg ttggtttttc ttttttcagc ttccaaccct tgcagctttc caaaaataaa    1680
tcaaaccagc catcagggca ccgaaataat actactgcta ataagcagct tcgcctagac    1740
ttagataaac aacacttctg aggtaaactt tgccccggag gtctggagac actttttttaa    1800 tgtaacctgc ttactaataa ttactagact tcagtgcatt aaccctggaa atagatttta    1860
atagccaccc cttaaaacaa aagacatgaa aagataataa gaaaaaagtg ccgcaactat    1920
tatagaaaaa cacttggcag cctgcttcag cccaagctga ggccacctct agcctctgct    1980
aaagcccccc actcccaatg gtccccgcca accggataag agtgcgcgcg ggacccgcct    2040 tccccctctcg gcaccgcccc cgccccgccc ccctcggctc gcctcccgcg tggctcctcc    2100
cttttccgct cctctcaacc tgactccagg agctggggtc aaattgctgg agcaggctga    2160
tttgcatagc ccaatggcca agctgcatgc aaatgaggcg gaaggtggtt ggctgagggt    2220
tggcaggata accccggaga gcggggcect ttgtcctcca gtggctggta ggcagtggct    2280
gggaggcagc ggcccaatta gtgtcgtgcg gcccgtggcg aggcgaggtc cggggagcga    2340
gcgagcaagc aaggcgggag gggtggccgg agctgcggcg gctggcacag gaggaggagc    2400
ccgggcgggc gaggggcggc cggagagcgc caggcctga gctgccggag cggcgcctgt    2460
gagtgagtgc agaaagcagg cgcccgcgcg ctagccgtgg caggagcagc ccgcacgccg    2520
cgctctctcc ctgggcgacc tgcagttttgc aatatggcgc gcctggtgag caagggcgag    2580
gagctgttca ccggggtggt gcccatcctg gtcgagctgg acggcgacgt aaacggccac    2640
aagttcagcg tgtccggcga gggcgagggc gatgccacct acggcaagct gaccctgaag    2700
ttcatctgca ccaccggcaa gctgcccgtg ccctggccca ccctcgtgac caccctgacc    2760
tacggcgtgc agtgcttcag ccgctacccc gaccacatga gcagcacga cttcttcaag    2820 tccgccatgc ccgaaggcta cgtccaggag cgcaccatct tcttcaagga cgacggcaac    2880
tacaagaccc gcgccgaggt gaagttcgag ggcgacaccc tggtgaaccg catcgagctg    2940
aagggcatcg acttcaagga ggacggcaac atcctggggc acaagctgga gtacaactac    3000
aacagccaca cgtctatat catggccgac aagcagaaga acggcatcaa ggtgaacttc    3060
aagatccgcc acaacatcga ggacggcagc gtgcagctcg ccgaccacta ccagcagaac    3120
acccccatcg gcgacggccc cgtgctgctg cccgacaacc actacctgag cacccagtcc    3180
gccctgagca agacccccaa cgagaagcgc gatcacatgg tcctgctgga gttcgtgacc    3240
gccgccggga tcactctcgg catggacgag ctgtacaagt aaagcggccg cgactctaga    3300
tcataatcag ccataccaca tttgtagagg ttttacttgc tttaaaaaac ctcccacacc    3360
tccccctgaa cctgaaacat aaaatgaatg caattgttgt tgttatcgcg accccgataa    3420
cgtggtgttg tgcctgctgg cggcggacga ggacgacgac agagatgtgg ctctgcagat    3480
```

```
ccacttcacc ctgatccagg cgttttgctg cgagaacgac atcaacatcc tgcgcgtcag    3540
caacccgggc cggctggcgg agctcctgct cttggagacc gacgctggcc ccgcggcgag    3600
cgagggcgcc gagcagcccc cggacctgca ctgcgtgctg gtgacggtaa gggactgggg    3660
gactgcagcc tgcagggtag agccccggaa ggacgggagt cagggctggg ttgcctgatt    3720
gtggatctgt ggtaggtggg ggtcaggagg gtggctgcct ttgtccgact agagtgtggc    3780
tggactttca gccgagatgt gctagtttca tcaccaggat tttctgtggt acagaacatg    3840
tctaagcatg ctggggactg ccagcagcgg aagagatccc tgtgagtcag cagtcagccc    3900
agctactccc tacctacatc tgcactgcct cccgtgacta attcctttag cagggcagat    3960
tagataaagc caaatgaatt cctggctcac ccctcattaa ggagtcagct tcattctctg    4020
ccagtcagag ctaaaaatag aaattgtgta ggagacaaac cttgttaatt ccctagaaat    4080
acattaagag gatagagtgg aattttttt ctctgcaatc ttgcattttt ttaatggctc    4140
tttttttttt tcctgataaa aacctttggt aggtagggaa gttatgtttt cagggggtaaa    4200 tgtgctactt ttgtcttcta aattttgctc ttttttgact ggtctagtca agtgacagcc    4260
cgattatttt gctactcctt aaaagtacta ttctgtctct tggagtatgg ttgatggcaa    4320
ttccagttaa ctgctgtgca gctctcatct cattgtgcac acagcatgga aatctttctc    4380
aaaactgttt cactcaggtc agggtaacaa gtttggtaga gcaaaccggt gaatgatact    4440
ctcatgcaaa actgaacaga tatgcaaaca tatgtatgtg gttcagcttg ggttgcatgg    4500
gttcagactt tgcaatgtgt agtttaatag gtaattaccc ttaacgcttt tgcagggaac    4560
ccaactacct tgaagaaact ttaatttttt tgtgcttcta atttgtctcc atgtcacata    4620
gccaaaatat agaatgttca agtgttttct cctcaaaagt ataattacta gaatatactg    4680
gtttttaaaa taagtttatt tttataaatt tgtttccaga atccacattc atctcaatgg    4740
aaggatcctg ccttaagtca acttattgt ttttgccggg aaagtcgcta catggatcaa    4800
tgggttccag tgattaatct ccctgaacgg tgatggcatc tgaatgaaaa taactgaacc    4860
aaattgcact gaagtttttg aaataccttt gtagttactc aagcagttac tccctacact    4920
gatgcaagga ttacagaaac tgatgccaag gggctgagtg agttcaacta catgttctgg    4980
gggcccggag atagatgact ttgcagatgg aaagaggtga aatgaagaa ggaagctgtg    5040 ttgaaacaga aaataagtc aaaaggaaca aaaattacaa agaaccatgc aggaaggaaa    5100
actatgtatt aatttagaat ggttgagtta cattaaaata aaccaaatat gttaaagttt    5160
aagtgtgcag ccatagtttg ggtattttg gtttatatgc cctcaagtaa aagaaaagcc    5220
gaaagggtta atcatatttg aaaaccatat tttattgtat tttgatgaga tattaaattc    5280
tcaaagtttt attataaatt ctactaagtt atttatgac atgaaaagtt atttatgcta    5340
taaatttttt gaaacacaat acctacaata aactggtatg aataattgca tcatttctta    5400
ttgtgtgctc g                                                         5411
```

<210> SEQ ID NO 4
<211> LENGTH: 5413
<212> TYPE: DNA
<213> ORGANISM: Homo sapiens
<220> FEATURE:
<221> NAME/KEY: GADD45alpha promoter
<222> LOCATION: (4)..(2254)
<223> OTHER INFORMATION:
<220> FEATURE:
<221> NAME/KEY: GADD45alpha 5' UTR
<222> LOCATION: (2255)..(2549)

```
<223> OTHER INFORMATION:
<220> FEATURE:
<221> NAME/KEY: EGFP gene
<222> LOCATION: (2550)..(3278)
<223> OTHER INFORMATION:
<220> FEATURE:
<221> NAME/KEY: SV40 polyA
<222> LOCATION: (3432)..(3482)
<223> OTHER INFORMATION:
<220> FEATURE:
<221> NAME/KEY: GADD45alpha Exon 3
<222> LOCATION: (3502)..(3642)
<223> OTHER INFORMATION:
<220> FEATURE:
<221> NAME/KEY: GADD45alpha Intron 3
<222> LOCATION: (3643)..(4715)
<223> OTHER INFORMATION:
<220> FEATURE:
<221> NAME/KEY: p53 motif
<222> LOCATION: (3830)..(3849)
<223> OTHER INFORMATION:
<220> FEATURE:
<221> NAME/KEY: AP-1 motif
<222> LOCATION: (3879)..(3885)
<223> OTHER INFORMATION:
<220> FEATURE:
<221> NAME/KEY: GADD45alpha Exon 4
<222> LOCATION: (4716)..(5391)
<223> OTHER INFORMATION:
<220> FEATURE:
<221> NAME/KEY: GADD45alpha 3' UTR
<222> LOCATION: (4830)..(5391)
<223> OTHER INFORMATION:

<400> SEQUENCE: 4
```

| | | | | | |
|---|---|---|---|---|---|
| atcagatctt | gggtgggggca | ctttaggact | gtggttcatt | tgaattggtg | taaacaatac | 60 |
| accggttcta | ctgtcctaca | gcctccattc | agatgactga | agtcatggga | ctttcagcat | 120 |
| agctagctga | tgacagtgca | tactattttg | tcccaaaatc | cagttcaagc | atggacatac | 180 |
| caataagagc | ctaagctctt | taaaggcaaa | ggaccaggaa | ttgtacagtt | cttggtatag | 240 |
| aagaagacag | gcaaaagtgt | ttttgaacta | acgttaaatg | tgcaatatgt | tagaattcat | 300 |
| gcaatgcaca | ggactgcagg | attctgatat | cttatttaac | tctcaaattc | tattcaactc | 360 |
| aataaacctt | gactgtgctt | ctactaaatg | caggtattgt | actaggagct | gaggacacca | 420 |
| aactgatgaa | gtccttgctg | tcaagaaact | cacatgattc | cctaattctt | tgtcagcttg | 480 |
| ctgtgatcac | atttttcttcc | caagaacctc | taagaaatgc | ctagtggata | gaaccttgga | 540 |
| gttccacgga | acatattaac | aatcgccaaa | tgatgactca | ggctagattg | tgtaattcag | 600 |
| gttttgtctg | caaaactgaa | aatgcttcgg | taacctacct | aaatttcaat | gttgaggaat | 660 |
| tctttaagaa | agacatcaaa | tgttaagatt | taaggcatag | atatgagata | catagtcatg | 720 |
| cttaggtgaa | ttatgcactg | accatgacca | tttctttact | caaatgttgt | ccatggctga | 780 |
| caacacagtg | aaaaaatgag | tgcaaaatga | caactcaaat | aaatgaacca | gaaaacctat | 840 |
| cacttttctt | ttccaccaaa | ttaagatcaa | gagagctgga | gaatattttg | tctagagtga | 900 |
| taaaaacata | agggtgcaaa | acttccaggt | acctttgcag | aaattacttc | tgtgaccttt | 960 |
| ggctgtacag | caaccttaat | aatgcaagca | ctgttttgaa | tgcaagcatg | tgggagccat | 1020 |
| tttcaccact | tttgatgact | tcagtaggtt | taagaaatgt | ttttgctttt | attgcataaa | 1080 |
| ccataaaaca | aaggaaggga | cttttgaact | actcagtgag | agtctatata | ttaaagtttg | 1140 |
| ttttcaaaa | atgtgtaact | accatttgca | gttttaaagg | tctgctttcc | acctacaagt | 1200 |
| tgccattatc | tcaaaggtga | aatttttagca | tatgactaaa | aacttcctat | agttacagct | 1260 |
| tcatgattca | gcatctaaca | tcaataattc | acagtgagat | cataggaggc | tctctgtgga | 1320 |

```
aggtaacgac atacatacgt taggaaagga agcttagggc atatcgagag cattttgaat    1380
ttagacttgt gggctgtgtg ggtgtcagat ggttgtctct cagctggtgg gcgtccagaa    1440
ggatccttgt ttgggcaagg ctctttgaga aaggagaatc tgggttgcca gggattccca    1500
catgtggtca ccagctcccc acgcagacca gctcacgatt tcccagttac accgggcagg    1560
tgggaaaccg ttctgctttc tgtggaaaag attctaactt ggttccctgc catccctgaa    1620
tacaaacggg ttggtttttc tttttcagc ttccaaccct tgcagctttc caaaaataaa     1680
tcaaaccagc catcagggca ccgaaataat actactgcta ataagcagct tcgcctagac    1740
ttagataaac aacacttctg aggtaaactt tgccccggag gtctggagac acttttttaa    1800
tgtaacctgc ttactaataa ttactagact tcagtgcatt aaccctggaa atagattta    1860 atagccaccc cttaaaacaa aagacatgaa aagataataa gaaaaaagtg ccgcaactat    1920
tatagaaaaa cacttggcag cctgcttcag cccaagctga ggccacctct agcctctgct    1980
aaagcccccc actcccaatg gtccccgcca accggataag agtgcgcgcg ggacccgcct    2040 tccccctctcg gcaccgcccc cgccccgcc cctcggctc gcctccgcg tggctcctcc     2100 cttttccgct cctctcaacc tgactccagg agctggggtc aaattgctgg agcaggctga    2160
tttgcatagc ccaatggcca agctgcatgc aaatgaggcg gaaggtggtt ggctgagggt    2220
tggcaggata accccggaga gcggggcct ttgtcctcca gtggctggta ggcagtggct     2280
gggaggcagc ggcccaatta gtgtcgtgcg gcccgtggcg aggcgaggtc cggggagcga    2340
gcgagcaaga aaggcgggag gggtggccgg agctgcggcg gctggcacag gaggaggagc    2400
ccgggcgggc gaggggcggc cggagagcgc cagggcctga gctgccggag cggcgcctgt    2460
gagtgagtgc agaaagcagg cgcccgcgcg ctagccgtgg caggagcagc ccgcacgccg    2520
cgctctctcc ctgggcgacc tgcagttttgc aatatggcgc gcctggtgag caagggcgag    2580
gagctgttca ccggggtggt gcccatcctg gtcgagctgg acggcgacgt aaacggccac    2640
aagttcagcg tgtccggcga gggcgagggc gatgccacct acggcaagct gaccctgaag    2700
ttcatctgca ccaccggcaa gctgcccgtg ccctggccca ccctcgtgac caccctgacc    2760
tacggcgtgc agtgcttcag ccgctacccc gaccacatga agcagcacga cttcttcaag    2820
tccgccatgc ccgaaggcta cgtccaggag cgcaccatct tcttcaagga cgacggcaac    2880
tacaagaccc gcgccgaggt gaagttcgag ggcgacaccc tggtgaaccg catcgagctg    2940
aagggcatcg acttcaagga ggacggcaac atcctggggc acaagctgga gtacaactac    3000
aacagccaca acgtctatat catggccgac aagcagaaga acggcatcaa ggtgaacttc    3060
aagatccgcc acaacatcga ggacggcagc gtgcagctcg ccgaccacta ccagcagaac    3120
acccccatcg gcgacggccc cgtgctgctg cccgacaacc actacctgag cacccagtcc    3180
gccctgagca agacccccaa cgagaagcgc gatcacatgg tcctgctgga gttcgtgacc    3240
gccgccggga tcactctcgg catggacgag ctgtacaagt aaagcggccg cgactctaga    3300
tcataatcag ccataccaca tttgtagagg ttttacttgc tttaaaaaac ctcccacacc    3360
tccccctgaa cctgaaacat aaaatgaatg caattgttgt tgttaacttg tttattgcag    3420
cttataatgg ttacaaataa agcaatagca tcacaaattt cacaaataaa gcatttttt    3480 cactgcattc tagttgttaa ttaattgctg cgagaacgac atcaacatcc tgcgcgtcag    3540
caacccgggc cggctggcgg agctcctgct cttggagacc gacgctggcc ccgcggcgag    3600
cgagggcgcc gagcagcccc cggacctgca ctgcgtgctg gtgacggtaa gggactgggg    3660
```

```
gactgcagcc tgcagggtag agccccggaa ggacgggagt cagggctggg ttgcctgatt    3720
gtggatctgt ggtaggtggg ggtcaggagg gtggctgcct ttgtccgact agagtgtggc    3780
tggactttca gccgagatgt gctagtttca tcaccaggat ttttctgtggt acagaacatg   3840 tctaagcatg ctggggactg ccagcagcgg aagagatccc tgtgagtcag cagtcagccc    3900
agctactccc tacctacatc tgcactgcct cccgtgacta attcctttag cagggcagat    3960
tagataaagc caaatgaatt cctggctcac ccctcattaa ggagtcagct tcattctctg    4020
ccagtcagag ctaaaaatag aaattgtgta ggagacaaac cttgttaatt ccctagaaat    4080
acattaagag gatagagtgg aattttttt ctctgcaatc ttgcattttt ttaatggctc     4140
tttttttttt tcctgataaa aacctttggt aggtagggaa gttatgtttt caggggtaaa    4200
tgtgctactt ttgtcttcta aattttgctc tttttttgact ggtctagtca agtgacagcc   4260
cgattatttt gctactcctt aaaagtacta ttctgtctct tggagtatgg ttgatggcaa    4320
ttccagttaa ctgctgtgca gctctcatct cattgtgcac acagcatgga aatctttctc    4380
aaaactgttt cactcaggtc agggtaacaa gtttggtaga gcaaaccggt gaatgatact    4440
ctcatgcaaa actgaacaga tatgcaaaca tatgtatgtg gttcagcttg ggttgcatgg    4500
gttcagactt tgcaatgtgt agtttaatag gtaattaccc ttaacgcttt tgcagggaac    4560
ccaactacct tgaagaaact ttaatttttt tgtgcttcta atttgtctcc atgtcacata    4620
gccaaaatat agaatgttca agtgttttct cctcaaaagt ataattacta gaatatactg    4680 gttttttaaaa taagtttatt tttataaatt tgtttccaga atccacattc atctcaatgg   4740
aaggatcctg ccttaagtca acttatttgt ttttgccggg aaagtcgcta catggatcaa    4800
tgggttccag tgattaatct ccctgaacgg tgatggcatc tgaatgaaaa taactgaacc    4860
aaattgcact gaagttttg aaatacctt gtagttactc aagcagttac tccctacact     4920
gatgcaagga ttacagaaac tgatgccaag gggctgagtg agttcaacta catgttctgg    4980
gggcccggag atagatgact ttgcagatgg aaagaggtga aaatgaagaa ggaagctgtg    5040
ttgaaacaga aaaataagtc aaaaggaaca aaaattacaa agaaccatgc aggaaggaaa    5100
actatgtatt aatttagaat ggttgagtta cattaaaata aaccaaatat gttaaagttt    5160
aagtgtgcag ccatagtttg ggtattttg gtttatatgc cctcaagtaa aagaaaagcc     5220
gaaagggtta atcatatttg aaaaccatat tttattgtat tttgatgaga tattaaattc    5280
tcaaagtttt attataaatt ctactaagtt attttatgac atgaaaagtt atttatgcta    5340
taaatttttt gaaacacaat acctacaata aactggtatg aataattgca tcatttctta    5400
ttgtgtgctc gag                                                       5413
```

<210> SEQ ID NO 5
<211> LENGTH: 3871
<212> TYPE: DNA
<213> ORGANISM: Homo sapiens
<220> FEATURE:
<221> NAME/KEY: GADD45alpha promoter
<222> LOCATION: (4)..(2254)
<223> OTHER INFORMATION:
<220> FEATURE:
<221> NAME/KEY: GADD45alpha 5' UTR
<222> LOCATION: (2255)..(2549)
<223> OTHER INFORMATION:
<220> FEATURE:
<221> NAME/KEY: EGFP gene
<222> LOCATION: (2550)..(3278)
<223> OTHER INFORMATION:
<220> FEATURE:
<221> NAME/KEY: GADD45alpha 3' UTR

```
<222> LOCATION: (3288)..(3849)
<223> OTHER INFORMATION:

<400> SEQUENCE: 5
atcagatctt gggtggggca ctttaggact gtggttcatt tgaattggtg taaacaatac      60
accggttcta ctgtcctaca gcctccattc agatgactga agtcatggga ctttcagcat     120
agctagctga tgacagtgca tactattttg tcccaaaatc cagttcaagc atggacatac     180
caataagagc ctaagctctt taaaggcaaa ggaccaggaa ttgtacagtt cttggtatag     240
aagaagacag gcaaaagtgt ttttgaacta acgttaaatg tgcaatatgt tagaattcat     300
gcaatgcaca ggactgcagg attctgtatat cttatttaac tctcaaattc tattcaactc     360
aataaacctt gactgtgctt ctactaaatg caggtattgt actaggagct gaggacacca     420
aactgatgaa gtccttgctg tcaagaaact cacatgattc cctaattctt tgtcagcttg     480
ctgtgatcac attttcttcc caagaacctc taagaaatgc ctagtggata gaaccttgga     540
gttccacgga acatattaac aatcgccaaa tgatgactca ggctagattg tgtaattcag     600
gttttgtctg caaaactgaa aatgcttcgg taacctacct aaatttcaat gttgaggaat     660
tctttaagaa agacatcaaa tgttaagatt taaggcatag atatgagata catagtcatg     720
cttaggtgaa ttatgcactg accatgacca tttctttact caaatgttgt ccatggctga     780
caacacagtg aaaaaatgag tgcaaaatga caactcaaat aaatgaacca gaaaacctat     840 cactttttctt ttccaccaaa ttaagatcaa gagagctgga gaatattttg tctagagtga     900
taaaaacata agggtgcaaa acttccaggt acctttgcag aaattacttc tgtgaccttt     960
ggctgtacag caaccttaat aatgcaagca ctgttttgaa tgcaagcatg tgggagccat    1020
tttcaccact tttgatgact tcagtaggtt taagaaatgt ttttgctttt attgcataaa    1080
ccataaaaca aaggaaggga cttttgaact actcagtgag agtctatata ttaaagtttg    1140
tttttcaaaa atgtgtaact accatttgca gttttaaagg tctgctttcc acctacaagt    1200
tgccattatc tcaaaggtga aattttagca tatgactaaa aacttcctat agttacagct    1260
tcatgattca gcatctaaca tcaataattc acagtgagat cataggaggc tctctgtgga    1320
aggtaacgac atacatacgt taggaaagga agcttagggc atatcgagag cattttgaat    1380
ttagacttgt gggctgtgtg ggtgtcagat ggttgtctct cagctggtgg gcgtccagaa    1440
ggatccttgt ttgggcaagg ctctttgaga aaggagaatc tgggttgcca gggattccca    1500
catgtggtca ccagctcccc acgcagacca gctcacgatt tcccagttac accgggcagg    1560
tgggaaaccg ttctgctttc tgtggaaaag attctaactt ggttccctgc catccctgaa    1620
tacaaacggg ttggtttttc ttttttcagc ttccaaccct tgcagctttc caaaaataaa    1680 tcaaccagc catcagggca ccgaaataat actactgcta ataagcagct cgcctagac    1740 ttagataaac aacacttctg aggtaaactt tgccccggag gtctggagac actttttaa    1800 tgtaacctgc ttactaataa ttactagact tcagtgcatt aaccctggaa atagatttta    1860
atagccaccc cttaaaacaa aagacatgaa aagataataa gaaaaaagtg ccgcaactat    1920
tatagaaaaa cacttggcag cctgcttcag cccaagctga ggccacctct agcctctgct    1980 aaagccccccc actcccaatg gtccccgcca accgataaag agtgcgcgcg ggacccgcct    2040
tcccctctcg gcaccgcccc cgccccgcc ccctcggctc gcctcccgcg tggctcctcc    2100
cttttccgct cctctcaacc tgactccagg agctggggtc aaattgctgg agcaggctga    2160
tttgcatagc ccaatggcca agctgcatgc aaatgaggcg gaaggtggtt ggctgagggt    2220
```

```
tggcaggata accccggaga gcggggccct ttgtcctcca gtggctggta ggcagtggct    2280
gggaggcagc ggcccaatta gtgtcgtgcg gcccgtggcg aggcgaggtc cggggagcga    2340
gcgagcaagc aaggcgggag gggtggccgg agctgcggcg gctggcacag gaggaggagc    2400
ccgggcgggc gaggggcggc cggagagcgc cagggcctga gctgccggag cggcgcctgt    2460
gagtgagtgc agaaagcagg cgcccgcgcg ctagccgtgg caggagcagc ccgcacgccg    2520
cgctctctcc ctgggcgacc tgcagtttgc aatatggcgc gcctggtgag caagggcgag    2580
gagctgttca ccggggtggt gcccatcctg gtcgagctgg acggcgacgt aaacggccac    2640
aagttcagcg tgtccggcga gggcgagggc gatgccacct acggcaagct gaccctgaag    2700
ttcatctgca ccaccggcaa gctgcccgtg ccctggccca ccctcgtgac cacccctgacc   2760 tacggcgtgc agtgcttcag ccgctacccc gaccacatga agcagcacga cttcttcaag    2820
tccgccatgc ccgaaggcta cgtccaggag cgcaccatct tcttcaagga cgacggcaac    2880
tacaagaccc gcgccgaggt gaagttcgag ggcgacaccc tggtgaaccg catcgagctg    2940
aagggcatcg acttcaagga ggacggcaac atcctggggc acaagctgga gtacaactac    3000
aacagccaca acgtctatat catggccgac aagcagaaga acggcatcaa ggtgaacttc    3060
aagatccgcc acaacatcga ggacggcagc gtgcagctcg ccgaccacta ccagcagaac    3120 accccatcg gcgacggccc cgtgctgctg cccgacaacc actacctgag cacccagtcc    3180
gccctgagca agacccccaa cgagaagcgc gatcacatgg tcctgctgga gttcgtgacc    3240
gccgccggga tcactctcgg catggacgag ctgtacaagt aaagcggccg ctggcatctg    3300
aatgaaaata actgaaccaa attgcactga agtttttgaa atacctttgt agttactcaa    3360
gcagttactc cctacactga tgcaaggatt acagaaactg atgccaaggg gctgagtgag    3420
ttcaactaca tgttctgggg gcccggagat agatgacttt gcagatggaa agaggtgaaa    3480
atgaagaagg aagctgtgtt gaaacagaaa aataagtcaa aaggaacaaa aattacaaag    3540
aaccatgcag gaaggaaaac tatgtattaa tttagaatgg ttgagttaca ttaaaataaa    3600
ccaaatatgt taaagtttaa gtgtgcagcc atagtttggg tattttggt  ttatatgccc    3660 tcaagtaaaa gaaaagccga aagggttaat catatttgaa aaccatattt tattgtattt    3720
tgatgagata ttaaattctc aaagttttat tataaattct actaagttat tttatgacat    3780
gaaaagttat ttatgctata aatttttga aacacaatac ctacaataaa ctggtatgaa     3840
taattgcatc atttcttatt gtgtgctcga g                                    3871
```